United States Patent [19]

Grudzinskas

[11] 4,206,151
[45] Jun. 3, 1980

[54] 15-DEOXY-16-HYDROXY-16-VINYL OR CYCLOPROPYL PROSTAN-1-OLS OF THE E, A AND F SERIES

[75] Inventor: Charles V. Grudzinskas, Nyack, N.Y.

[73] Assignee: American Cyanamid Company, Stamford, Conn.

[21] Appl. No.: 972,005

[22] Filed: Dec. 21, 1978

[51] Int. Cl.² .................... C07C 44/28; C07C 35/06
[52] U.S. Cl. .................... 568/367; 260/345.8 P; 260/345.4 P; 260/438.1; 260/463; 260/429.7; 560/18; 560/72; 560/106; 560/107; 560/162; 560/231; 568/591; 568/816; 568/838; 424/331; 424/343; 556/482; 556/485; 556/436; 568/379; 556/427; 556/441

[58] Field of Search ........ 260/586 R, 617 R, 444.8 R, 260/345.8 P, 345.9 P, 463; 568/591, 838, 816; 560/231, 162, 106, 107, 72, 18

[56] References Cited

U.S. PATENT DOCUMENTS

4,132,738   1/1979   Kluender et al. ................ 260/586 R

*Primary Examiner*—Robert Gerstl
*Attorney, Agent, or Firm*—Richard J. Hammond

[57] ABSTRACT

This disclosure describes novel 15-deoxy-16 hydroxy-16-substituted prostanoic acid analogs in which the C-1 carboxyl is replaced by a primary alcohol and carboxylic acid esters, carbonates and carbomates thereof. The prostanoic carbinols and carboxylic acid esters thereof described herein have utility as bronchodilators as hypotensive agents, and as agents for the control of excessive gastric secretion.

37 Claims, No Drawings

15-DEOXY-16-HYDROXY-16-VINYL OR CYCLOPROPYL PROSTAN-1-OLS OF THE E, A AND F SERIES

BACKGROUND OF THE INVENTION (1) Field of the Invention

The present invention relates to 15-deoxy-16 hydroxy-16-vinyl and 16-cyclopropyl prostaglandins, as well as the pharmaceutically acceptable, non-toxic lower alkyl esters and salts thereof, and to the intermediates and processes for producing such compounds.

(2) Background of the Invention

Prostaglandins have classically been described as chemically related 20 carbon chain hydroxy fatty acids having the basic skeleton of prostanoic acid:

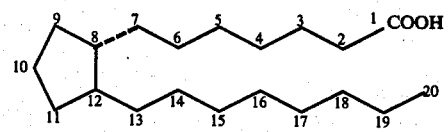

The prostaglandins having a hydroxyl group at the C-11 position and a keto group at the C-9 position are known as the PGE series, and those having a hydroxyl group in place of the keto group are known as the PGF series and are further designated by an α or β suffix to indicate the configuration of the hydroxyl group at said position. The natural compounds are the α-hydroxy substituted compounds. They may contain different degrees of unsaturation in the molecule, particularly at C-5, C-13 and C-17, the unsaturation is also indicated by a suffix. Thus, for example, the $PGF_1$ and $PGE_1$ series refer to prostanoic acids having a trans olefin bond at the C-13 position, while the $PGF_2$ and $PGE_2$ series refer to prostadienoic acids having a cis-olefin bond at the C-5 position and a trans olefin bond at the C-13 position. For a review on prostaglandins and the definition of primary prostaglandins, see, for example, S. Bergstrom, *Recent Progress in Hormone Research*, 22, 153–175 (1966) and *Science*, 157, 382 (1967) by the same author.

The preparation of derivatives of prostanoic acid has become of great importance since the demonstration of the highly interesting range of biological and pharmacological activities of natural prostaglandins.

The great majority of these studies have focused on modification of the two side chains, or modifications of the substituents attached to the cyclopentane moiety [see for example, U. Axes et al., Synthesis Vol. 1, John Wiley and Sons Inc., New York, N.Y. 1973 and P. H. Bently, Chem. Soc. Reviews, 2, 29 (1973)].

The synthesis of several prostaglandin analogs wherein the hydroxyl group at C-15 has been removed and a hydroxyl group has been introduced at C-16 has appeared [see for example, U.S. Patent No. 3,950,406; Prostaglandins, 10, 733 (1975); Tetrahedron Letters, 48, 4217 (1975)].

Recently reports have also appeared wherein the C-16 carbon bearing a hydroxyl group is substituted with a methyl group [see Pappo et al, Tetrahedron Letters, No. 4, 235 (1975); Collin et al, U.S. Pat. No. 3,965,143; and Belgium Patent No. 827,127].

Recently the synthesis of some PGE carbinols has been described (in U.S. Pats. No. 4,028,419, No. 4,088,691, No. 4,088,692, No. 4,088,693, No. 4,088,694). The synthesis of prostanols from the 1,4-conjugate addition to a cyclopentenone has been reported by Kluender et al., Tetrahedron Letters, No. 24, 2063–2066 (1977). These compounds exhibit more specific activities than natural PGE.

The 15-deoxy-16-hydroxy-16-vinyl and 16-cyclopropyl analogs of the E, F, A, and D series have been described in U.S. Pat. No. 4,061,670, the grandparent of this application.

BRIEF SUMMARY OF THE INVENTION

This invention relates to novel 15-deoxyl-16-hydroxy-16 substituted prostane-1-ols and congeners thereof, as well as to intermediates and methods for their preparation. The prostane-1-ols are prostanoic acid analogs in which the C-1 carboxyl is replaced by a primary alcohol or their esters.

The novel compounds of this invention embrace all the optical antipodes, racemic mixtures and diasteromeric mixtures corresponding to the following general formula, the absolute configuration is that of the natural mammalian prostaglandins.

The compounds of this invention may be represented by the following general formula and the mirror image thereof:

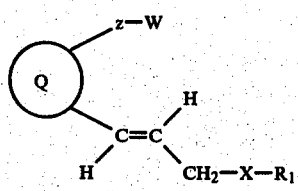

where Q is selected from the group comprising:

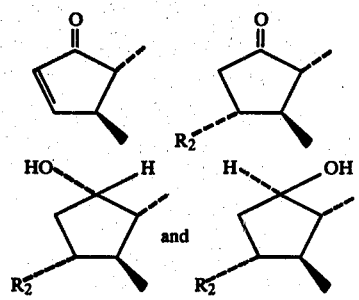

wherein $R_1$ is an alkyl or alkenylmethyl group ($C_3$–$C_7$) optionally substituted with one or two alkyl groups of one to three carbon atoms; $R_2$ is selected from the group comprising hydroxyl, alkanoyloxy ($C_2$–$C_6$), alkoxyalkoxy, wherein the alkyl group is ($C_1$–$C_6$), triloweralkyl silyloxy, tetrahydropyran-2-yloxy and alkoxy ($C_1$–$C_3$); X is the divalent radical

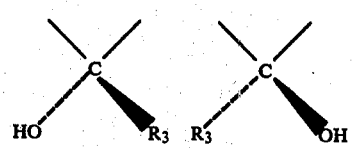

wherein $R_3$ is selected from the group comprising vinyl and cyclopropyl; Z is selected from the group comprising —$(CH_2)_4$, and

$-CH_2-CH\overset{Cis}{=}CH-CH_2-$, and W is selected from the group consisting of

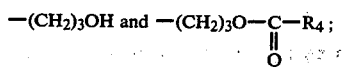

$-(CH_2)_3OH$ and $-(CH_2)_3O-\underset{\underset{O}{\parallel}}{C}-R_4$;

wherein $R_4$ is selected from the group comprising alkyl ($C_1$–$C_4$); dialkylamino ($C_1$–$C_4$); alkoxy ($C_1$–$C_4$); phenyl and phenyl substituted with one ore more substituents selected from the group consisting of hydrogen hydroxyl, alkyl ($C_1$–$C_4$), or -SR, fluoride or chloride, wherein R is ($C_1$–$C_4$) alkyl a preferred embodiment is wherein $R_2$ is hydroxy.

The dotted line shown in the above formula and in the formulas below indicate that the substituents are in α configuration, i.e. below the plane of the cyclopentenone ring.

These novel compounds possess asymmetric centers and thus can be produced as racemic mixtures or as individual enantiomers. The racemic mixtures can be resolved if desired at appropriate stages by methods known, to those skilled in the art, to obtain the respective individual enantiomers. It is to be understood that the racemic mixtures and the individual 8 R enantiomers are encompassed within the scope of the present invention.

When the compounds of the present invention are racemic mixtures, they are produced from precursors which are racemic, and when the compounds of the invention are individual enantiomers, the compounds are preferably obtained from appropriate individual enantiomers.

DETAILED DESCRIPTION OF THE INVENTION

The novel compounds of this invention can be prepared by a 1,4-conjugate-addition procedure involving treatment of the ether blocked cyclopentenone (15) with a lithio-cuprate reagent such as (9) or (13) prepared as illustrated in Flowcharts A, B, C, D, E, F, G, and H, in which $R_1$, $R_2$, $R_3$, $R_4$, W and n are as hereinabove described and $R_1'$, $R_2'$ is lower alkyl ($C_1$–$C_4$).

The requisite cyclopentenones of this invention may be prepared by a novel process from carboxy-3,4-alkene 2,5-dimethoxy furan typically represented as I according to Flowchart A.

FLOWCHART A

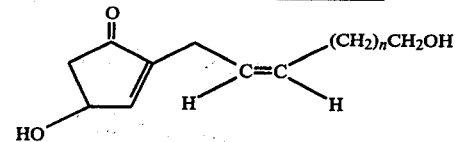

-continued
FLOWCHART A

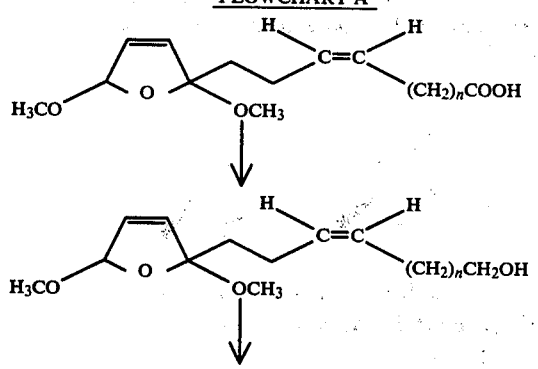

In accordance with the procedure outlined the carboxyl group on the side chain of 2,5-dimethoxy furan is reduced to an alcohol by the use of sodium bis-(2-methoxyethoxy) aluminum hydride. Subsequently, the product (II) is rearranged to form the required 4-hydroxycyclopentenone. The saturated side chain cyclopentenone has been prepared and the procedure is reported by Kluender and Peruzzotti, Tetrahedron Letters, No. 24, 2063–2066 (1977).

The hydroxyl moieties on the requisite cyclopentenone of this invention can be protected by silylation with chlorotrialkylsilane to provide the silyl ether as shown on Flowchart E as (15). Alternatively, the hydroxyl moieties may also be protected by using a 2-alkoxypropene such as 2-methoxy-propene or 2-ethoxyethylene according to the following Flowchart B

FLOWCHART B

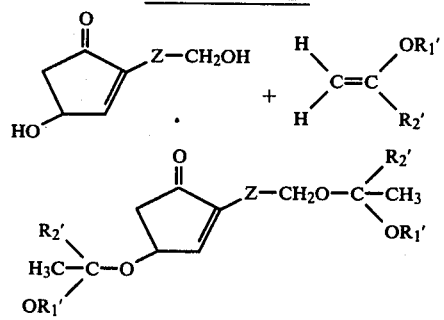

wherein $R_1'$ and $R_2'$ are defined as above. 2-alkoxypropene is added under pressure to a methylene chloride solution of the cyclopentenone at 10°–15° C. A few drops of dichloroacetic acid is added to the mixture. The solution is stirred and the alkoxyether is extracted into hexane.

Other useful protecting groups are tetrahydropyran, dihydro-2H-pyran, 2,2-dimethoxypropane, ethylvinyl ether and the like.

In accordance with the procedure as outlined in Flowchart C, an aldehyde (1) is treated with propargylic magnesium halide to form the homopropargylic alcohol (2) which is converted to its trimethylsilyl ether in the usual manner. The silylated derivative is then treated with diisoamylborane (prepared in situ in tetrahydrofuran solution at ice bath temperature from 2-methyl-2-butene, sodium borohydride and boron trifluoride etherate) and then anhydrous trimethylamine oxide. The resulting solution and an iodine solution in tetrahydrofuran are then added simultaneously to an aqueous solution of sodium hydroxide to give the 1-iodo-4-trimethylsilyloxy-trans-1-alkene (3).

The trimethylsilyl protecting group is removed with mild acid and the resulting vinyl iodide alcohol is oxidized with pyridinium chlorochromate to provide the 1-iodo-4-oxo-trans-1-alkene (4), which upon treatment with a Grignard reagent ($R_3MgX$) provides the 1-iodo- 4-hydroxy-trans-1-alkene, which is silylated in the usual manner to provide the silyl ether (8a).

Treatment of (8a) at low temperature, preferably −30° C. to −78° C. in an inert solvent, e.g. hexane, ether or toluene, with an alkyl lithium, e.g. n-butyl lithium or t-butyl lithium (2 equivalents) provides the trans-1-alkenyl lithium reagent (9).

A more preferred method for the preparation of the vinyllithium intermediate (9) is described in Flowchart D. Treatment of the requisite carboxylic acid (5 or 5a) with the appropriate organolithium reagent (R₁Li or R₃Li respectively) gives the corresponding ketone (6) which upon treatment with propargylic magnesium halide provides the homopropargylic alcohol (7) which is converted to the trans vinylstannyl derivative by sequential treatment with chlorotrimethylsilane and tri-n-butylstannyl hydride in the presence of azobisisobutryl-nitrile.

FLOWCHART C

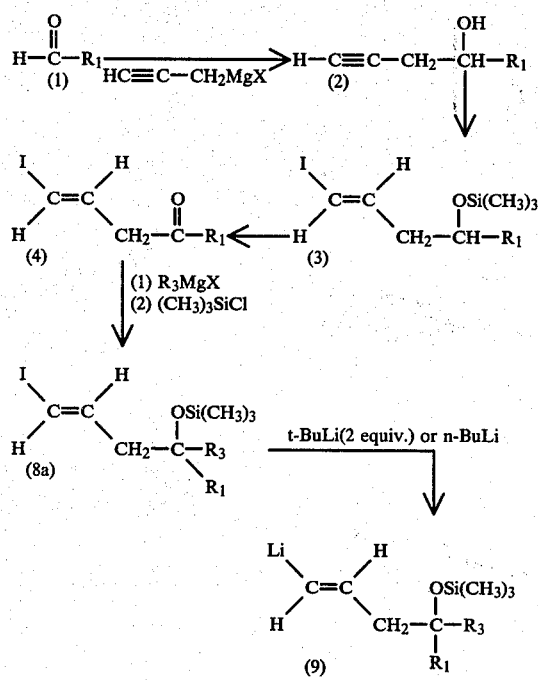

FLOWCHART D

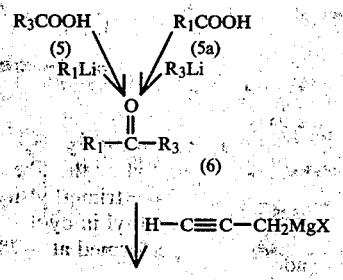

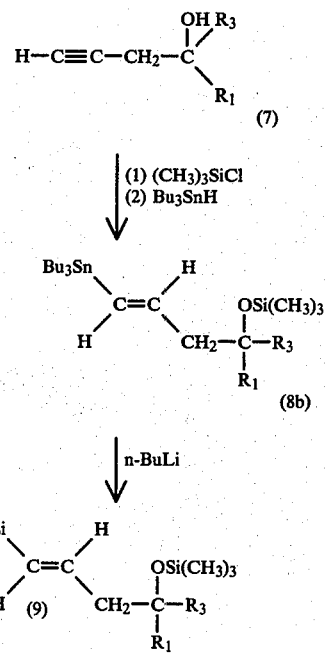

Treatment of the vinylstannyl reagent (8b) with n-butylithium at a temperature of −10° to −78° C. generates the vinyllithium reagent (9).

For the preparation of the asymmetrical lithio cuprate (10) or the like described in Flowchart E, a solution of one molar equivalent of copper (I)-1-alkyne, preferably copper (I)-1-pentyne in anhydrous tributylphosphine or HMPTA, preferably one to five molar equivalents in ether is added to one molar equivalent of the aforementioned vinyl-lithium solution cooled to about −78° C. After about one hour at this temperature, a molar equivalent of the requisite cyclopentenone (15) is added. After several hours at −30° C. to −70° C. the reaction mixture is quenched with aqueous ammonium chloride solution and the blocked product (16) is isolated in the usual manner.

It is also possible to effect conjugate 1,4-addition with the asymmetrical lithio cuprate (12) derived from vinyl lithium (9) and cuprous thiophenoxide. A solution of vinyl lithium (9) in ether at −78° C. is reacted with an equimolar amount of a reagent prepared by admixture, in ether at a temperature of 0° C. to −78° C., of equimolar amounts of cuprous thiophenoxide and copper (I) iodide tributylphosphonium complex. After about 30 minutes at this temperature, the lithio cuprate (12) is treated with the requisite cyclopentenone (15) as described hereinabove for the conjugate addition with 1-alkynyl lithio cuprate (10).

FLOWCHART E

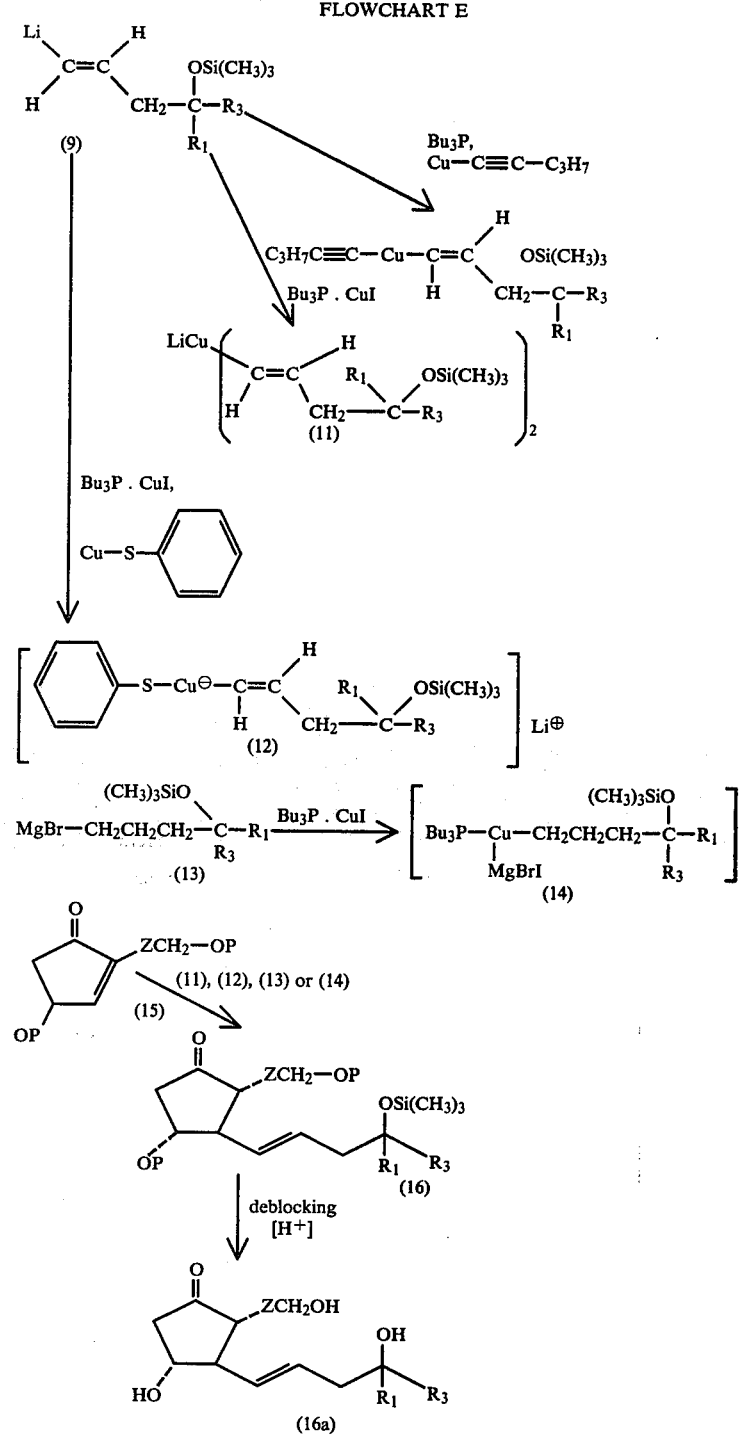

For the preparation of the symmetrical lithio cuprate (11) one molar equivalent of copper (I) iodide tributylphosphine complex, dissolved in anhydrous ether, is added at about −78° C. to two molar equivalents of the aforementioned vinyl lithium (9) solution in hexanes, cooled to −78° C. After about one hour at this temperature, the lithio cuprate (11) is treated with the requisite cyclopentenone (15) as described hereinabove for the conjugate addition with the 1-alkynyl lithio cuprate (10).

The procedures for conjugate addition involving organocopper reagents are well known in the art, see for example, C. J. Sih, et al., J. Amer. Chem. Soc., 97, 865 (1975).

Flowchart E describes such 1,4-conjugate additions, wherein $R_1$ and $R_3$ are as previously defined and P is a protecting group such as tetrahydropyranyl; tri lower alkylsilyl, preferably trimethylsilyl; 1-methoxyl-1-methylethyl; 1-ethoxyethyl or the like.

In the cases where P is=trimethylsilyl; 1-methoxy-1-methylethyl, 1-ethyloxyethyl in cyclopenteone (15) the conjugate addition is performed at −78° C. to −40° C.

The reaction is quenched by addition of an ether solution of acetic acid. Removal of blocking groups is then carried out as described in the reference above to provide the product (16a) wherein $R_1$, $R_3$ are as hereinabove defined and $R_2''$ is hydroxyl.

All available evidence leads us to believe that the

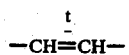

function introduced by the cuprate process occupies a position trans to the 11-oxy function. Similarly, we are led to the conclusion that in the product (14) the two side-chains attached to $C_8$ and $C_{12}$ are trans to each other. However, we are not certain of this configurational relationship in the product as it is obtained directly from the cuprate process. These products may have the sidechains in a trans- or cis-relationship or they may be a mixture containing both the trans- and cis-isomers. This is indicated in the nonenclature of the compounds involved by the designation 8$\epsilon$. In order to ensure a trans-relationship in (16) these products can be submitted to conditions known in the literature to equilibrate the cis-8-iso-PGE$_1$ to a mixture contining about 90% of the trans product. These conditions involve treatement with potassium acetate in aqueous methanol for 96 hours at room temperature.

The alkoxyalkoxyl substituted lithio-cuprate reagents of type (10) and its iodo and trialkylstannyl precursors are novel and useful compounds which are also embraced by this invention. The may be defined by generic formulae (A) and (B).

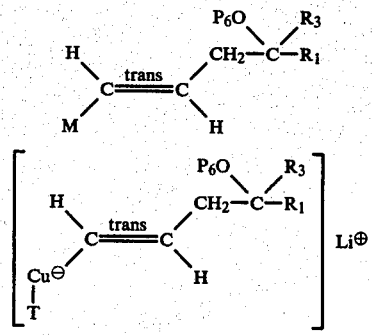

wherein M is iodine or tri n-butylstannyl, $R_1$ and $R_3$ are as hereinabove defined, $P_6$ is alkoxyalkyl, T is thiopheneoxide, substituted thiopheneoxide, as alkyne or the identical vinyl moiety.

The 13-dihydro derivatives can be prepared, as shown in Flowchart E, by treating cycloalkenones of formula (15) with Grignard reagent such as (13), in the usual manner in the presence of a catalyst such as the tributylphosphine-cuprous-iodide complex. The trimethylsilyl and other blocking groups are then removed in the usual manner as described hereinabove.

In accordance with Flowchart F, when the 11-hydroxy derivatives embraced by (17) are treated with dilute acid, or dilute base, it is possible to effect elimination and the formation of the corresponding $\Delta^{10}$ derivatives (18) prostaglandins of the A type. A preferred procedure involves treatment in tetrahydrofuran water (2:1) solvent with 0.5 N in HCl for about 70 hours at ambient temperatures or alternatively in methanol-water solvent (1:5) with 0.2 M potassium carbonate for 16 hours at ambient temperatures. Under acidic conditions, a tetrahydropyranyl or trialkylsilyl ester will undergo hydrolysis.

FLOWCHART F

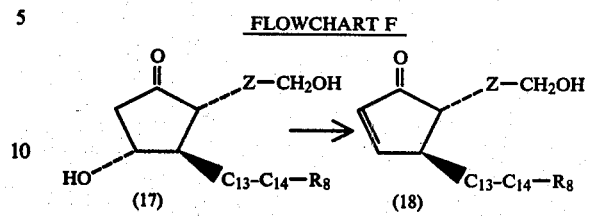

In Flowchart F, Z and $C_{13}$-$C_{14}$ are as hereinabove defined, $R_5$ is hydrogen or a lower alkyl ($C_1$-$C_6$) and $R_8$ is the moiety

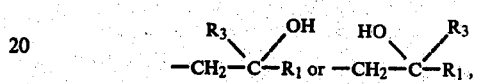

wherein $R_1$ and $R_3$ are as hereinabove described.

The 9-keto derivatives of this invention can be converted to the corresponding 9-hydroxy derivatives as described in Flowchart G. If this conversion is effected with sodium borohydride, the product is a mixture of 9$\alpha$- and 9$\beta$- hydroxy derivatives (19) and (20) respectively, as set forth in the following reaction scheme, wherein $R_2$, Z and $C_{13}$-$C_{14}$ are as herein above defined, and $R_8$ is the moiety

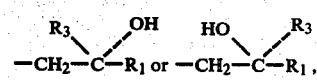

wherein $R_1$ and $R_3$ are as hereinabove defined.

FLOWCHART G

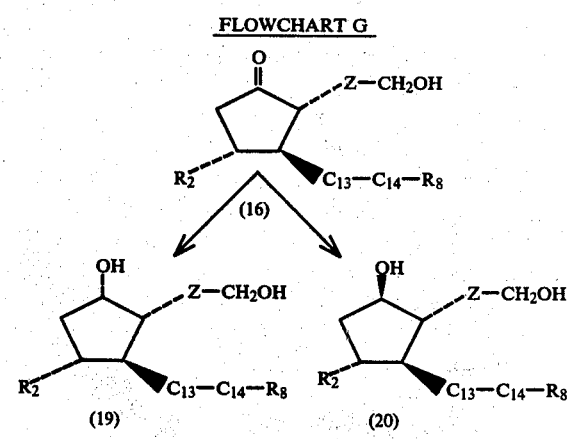

When the reaction is carried out with lithium perhydro-9b-boraphenylyl hydride [H. C. Brown and W. C. Dickason, J.A.C.S., 92, 709, (1970)] or lithium tris(t-butyl)-boro-hydride [H. C. Brown and S. Krishnamurthy, ibid., 94, 7159 (1972)] the product is at least predominantly the 9$\alpha$-hydroxy derivative (19) wherein the 9-hydroxy group is cis to the side chain attached to $C_8$.

FLOWCHART H

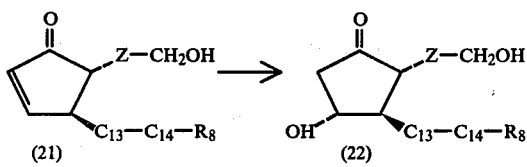

In accordance with Flowchart H, wherein Z, $R_8$, and $C_{13}$–$C_{14}$ are as described hereinabove, treatment of PGA analogs (21) with alkaline hydrogen peroxide to provide a mixture of 10, 11-epoxides which, without separation is reduced with chromous acetate in acidic media or by aluminum amalgam to provide after hydrolysis (if necessary) and silica gel chromatography the 11-hydroxy PGE compounds and a lesser amount of the corresponding 11β-epimer.

FLOWCHART I

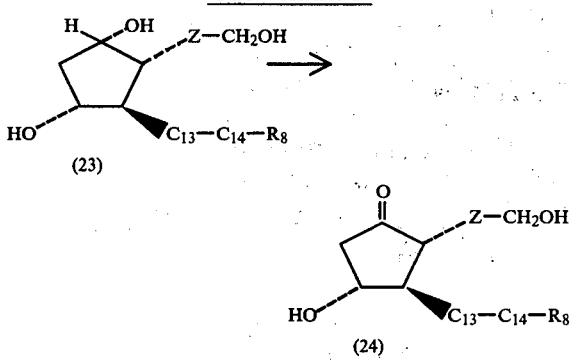

In accordance with Flowchart I wherein Z, $R_8$ and $C_{13}$–$C_{14}$ are as described hereinbelow, the PGF$_\alpha$ analogs (23) are treated with N-trimethylsilyldiethylamine according to the procedure of Yankee et al. J. Chem. Soc.: Chem. Comm., 1121 (1972). The resulting silated material is oxidized with Collen's agent in situ. The product is hydrolyzed and purified on silica gel to provide the PGE analogs (24).

The carbinols of this invention can be readily converted to the various esters by treatment with acetic anhydride in pyridine. The resulting 1-hydromethyl analogs are chromatographed and eluted from a silica gel column and subsequently converted to esters by reaction with the appropriate acid anhydrides or acyl halides to provide the esters of the prostanols (26). The procedure is described in Flowchart J, where Z, is as previously defined.

FLOWCHART J

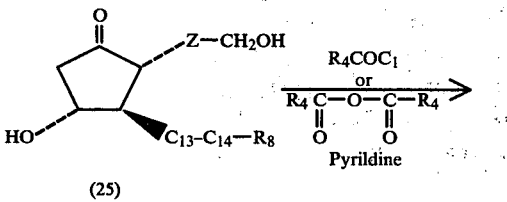

-continued
FLOWCHART J

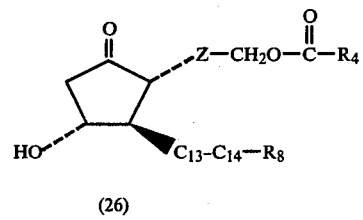

When the compounds of this invention are prepared from racemic starting compounds, two racemates are obtained. In appropriate instances these racemates may be separated from each other by careful application of the usual chromatographic procedures. In the more difficult instances it may be necessary to apply high pressure liquid chromatography including recycling techniques. [See G. Fallick, American Laboratory, 19–27 (August 1973) as well as references cited therein. Additional information concerning high speed liquid chromatography and the instruments necessary for its application is available from Waters Associate Inc., Maple Street, Milford, Mass.]

In the following formulae Z is as hereinabove defined.

The 4-hydroxycyclopentenone racemates may be resolved into their component enantiomers (23) and (24) wherein Z is as hereinabove defined by derivatizing the ketone function with a reagent having an optically active center. The resulting diastereoisomeric mixture can then be separated by fractional crystallization, or by chromatography, or by high speed liquid chromatography involving, if necessary, recycling techniques. Among the useful optically active ketone derivatizing reagents are 1-α-aminoxy-α-methylpentanoic acid hydrochloride (to give 25), (R)-2-aminoxy-3,3-dimethylbutyric acid hydrochloride, and 4-α-methylbenzyl semicarbazide. After separation of diastereomeric derivatives, reconstitution of the keto function provides the individual 4-hydroxycyclopentenone enantiomers (23) and (24). A useful procedure for the resolution of a 4-hydroxycyclopentenone racemate via an oxime such as (25) is described in the art [R. Pappo, P. Collins and C. Jung, Tetrahedron Letters, 943 (1973)]. The resolution of the hydroxycyclopentenone (25) wherein Z is

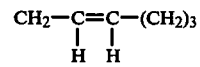

is described by Bruhn et al, Tetrahedron Letters, 235 (1976).

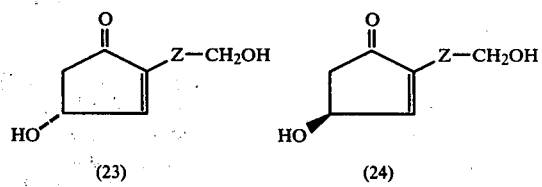

-continued

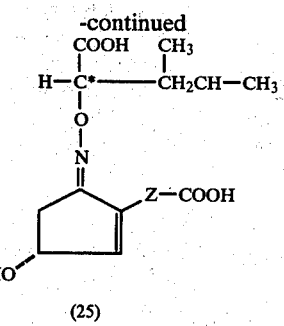

(25)

The novel compounds of the present invention have potential utility as hypotensive agents, anti-ulcer agents, agents for the treatment of gastric hypersecretion and gastric erosion, agents to provide protection against the ulcerogenic and other gastric difficulties associated with the use of various non-steroidal antiinflammatory agents (e.g., indomethacin, aspirin, and phenylbutazone), bronchodilators, antiinflammatory agents, abortifacients, agents for the induction of labor, agents for the induction of menses, fertility-controlling agents oestrus regulators for the use in animal husbandry with cattle and other domestic animals and central nervous system regulatory agents. Certain of the novel compounds of this invention possess utility as intermediates for the preparation of other of the novel compounds of this invention.

The ring system of certain of the novel compounds of this invention allow them to be characterized as follows:

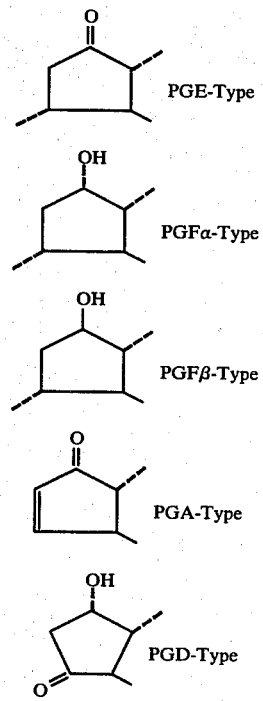

The novel compounds of this invention posses the pharmacological activity described below as associated with the appropriate above-described prostaglandin type.

The known PGE, $PGF_\alpha$, $PGF_\beta$, PGA and PGD compounds are all potent in causing multiple biological responses even at low doses. For example, $PGE_1$ and $PGE_2$ are extremely potent in causing vasodepression and smooth muscle stimulation, and also are potent as antilipolytic agents. Moreover, for many applications, these known prostaglandins have an inconveniently short duration of biological activity. In striking contrast, the novel prostaglandin analogs of this invention are substantially more specific with regard to potency in causing prostaglandin-like biological responses, and/or having a substantially, longer duration of biological activity. Therefore, each of these novel prostaglandin analogs is surprisingly and unexpectedly more useful than one of the corresponding above-mentioned known prostaglandins for at least one of the pharmacological purposes indicated below for the latter, either because it has a different and narrower spectrum of biological activity than the known prostaglandins, and therefore is more specific in its activity and causes smaller and fewer undesired side effects than the known prostaglandins, or because of its prolonged activity, fewer and smaller doses of the novel prostaglandin analog can frequently be used to attain the desired result.

The 11-deoxy-PGE, $PGF_\alpha$ and $PGF_\beta$ compounds are additionally selective in that they are at most relatively very weak, stimulants of smooth muscle. The 11-deoxy PGE compounds have a further advantage in that they are much more stable and have a longer "shelf-life" than the corresponding 11-hydroxy derivatives as described more fully hereinbelow.

Another advantage of the novel compounds of this invention, compared with the known prostaglandins, is that these novel compounds are administered effectively, orally, sublingually, intravaginally, buccally, or rectally, in addition to the usual intravenous, intramuscular, or subcutaneous injection or infusion methods indicated above the uses of the known prostaglandins. These qualities are advantageous because they facilitate maintaining uniform levels of these compounds in the body with fewer, shorter, or smaller doses, and make possible self-administration by the patient.

$PGE_1$, $PGE_2$, $PGE_3$ and dihydro-$PGE_1$, and the corresponding $PGF_\alpha$, $PGF_\beta$, and PGA, compounds, and their esters and pharmacologically acceptable salts, are extremely potent in causing various biological responses. For that reason, these compounds are useful for pharmacological purposes. See, for example, Bergstron, et al., Pharmacol. Rev., 20, 1 (1968), and references cited herein. A few of those biological responses are systemic arterial blood pressure lowering in the case of the PGE, $PGF_\beta$, and PGA compounds as measured, for example, in anesthetized phenobarbital sodium) pentolinium-treated rats with indwelling aortic and right heart cannulas; pressor activity, similarly measured, for the $PGF_\alpha$ compounds; stimulation of smooth muscle as shown, for example, by tests on strips of guinea pig ileum, rabbit duodenum, or gerbil colon; potentiation of other smooth muscle stimulants; antilipolytic activity as shown by antagonism of epinephrine-induced mobilization of free fatty acids or inhibition of spontaneous release of glycerol from isolated rat fat pads; inhibition of gastric secretion in the case of the PGE and PGA compounds as shown in dogs with secretion stimulated by food or histamine infusion; activity on the central nervous system; decrease of blood platelet adhesiveness in the case of PGE, as shown by platelet-to-glass adhesiveness, and inhibition of blood platelet aggregation and thrombus formation induced by various physical stimuli, e.g., arterial injury, and various biochemical stimuli, e.g., ADP, ATP, serotonin, thrombin, and collagen; and in the case of the PGE compounds, stimulation of epidermal proliferation and keratinization as shown when applied in culture to embryonic chick and rat skin segments.

Because of these biological responses, these known prostaglandins are useful to study, prevent, control, or alleviate a wide variety of diseases and undesirable physiological conditions in birds and mammals, including humans, useful domestic animals, pets, and zoological specimens, and in laboratory animals, for example, mice, rats, rabbits, and monkeys.

For example, these compounds, and especially the PGE compounds, are useful in mammals, including man, as nasal decongestants. For this purpose, the compounds are used in a dose range of about 10 μg to about 10 mg per ml of a pharmacologically suitable liquid vehicle or as an aerosol spray, both for topical application.

The PGE and PGA compounds are useful in mammals, including man and certain useful animals, e.g., dogs and pigs, to reduce and control excessive gastric secretion, thereby reducing or avoiding gastric erosion or gastrointestinal ulcer formation, and accelerating the healing of such ulcers already present in the gastrointestinal tract. For this purpose, the compounds are injected or infused intravenously, subcutaneously, or intramuscularly in an infusion dose range of about 500 mg to about 0.1 g per kg of body weight per minute, or in a total daily dose by injection or infusion in the range of about 0.1 mg to about 20 mg per kg of body weight per day, the exact dose depending on the age, weight, and condition of the patient or animal, and on the frequency and route of administration. These compounds may also be useful in conjunction with various non-steroidal antiinflammatory agents, such as aspirin, phenylbutazone, indomethacin and the like, to minimize the well-known ulcerogenic effects of the latter.

The $PGE_1$ and $PGD_2$ compounds are useful whenever it is desired to inhibit platelet aggregation, to reduce the adhesive character of platelets, and to remove or prevent the formation of thrombi in mammals, including man, rabbits, and rats. For example, these compounds are useful in treatment and prevention of myocardial infarcts, to treat and prevent post-operative thrombosis. For these purposes, these compounds are administered systemically, e.g., intravenously, subcutaneously, intramuscularly, and in the form of steril implants for prolonged action. For rapid response, especially in emergency situations, the intravenous route of administration is preferred. Doses in the range of about 0.005 mg to about 20 mg per kg of body weight per day are used, the exact dose depending on the age, weight, and condition of the patient or animal, and on the frequency and route of administration.

11α-Hydroxy-PGE compounds are extremely potent in causing stimulation of smooth muscle, and are also highly active in potentiating other known smooth muscle stimulators, for example, oxytocic agents, e.g., oxytocin, and the various ergot alkaloids including derivatives and analogs thereof. Therefore $PGE_2$, for example, is useful in place of or in combination with less than usual amounts of these known smooth muscle stimulators, for example to relieve the symptoms of paralytic ileus, or to control or prevent uterine bleeding after abortion or delivery, to aid in expulsion of the placenta, and during the puerperium. For the latter purpose, the PGE compound is administered by intravenous infusion immediately after abortion or delivery at a dose in the range about 0.01 μg to about 50 μg per kg of body weight per minute until the desired effect is obtained.

The PGE, $PGF_\beta$ and PGA compounds are useful as hypotensive agents to reduce blood pressure in mammals including man. For this purpose, the compounds are administered by intravenous infusion at the rate of about 0.01 μg to about 50 μg per kg of body weight per minute, or in a single or multiple doses of about 25 μg to 2500 μg per kg of body weight total per day.

The PGE, $PGF_\alpha$, and $PGF_\beta$ compounds are useful in place of oxytocin to induce labor in pregnant female animals, including man, cows, sheep, pigs, at or near term or in pregnant animals with intrauterine death of the fetus from about 20 weeks to term. For this purpose, the compound is infused intravenously at a dose 0.01 μg to 50 μg per kg of body weight per minute until or near the termination of the second stage of labor, i.e., expulsion of the fetus. These compounds are especially useful when the female is one or more weeks post-mature and natural labor has not started, or 12 to 60 hours after the membranes have ruptured and natural labor has not yet started.

The PGE, $PGF_\alpha$, and $PGF_\beta$ compounds are useful for controlling the reproductive cycle in ovulating femal mammals, including humans and other animals. For that purpose, $PGF_{2\alpha}$, for example, is administered systemically at a dose level in the range of 0.01 mg to about 20 mg per kg of body weight, advantageously during a span of time starting approximately at the time of ovulation and ending approximately at the time of menses or just prior to menses. Additionally, explusion of an embryo or fetus is accomplished by similar administration of the compound during the first third or the second third of the normal mammalian gestation period. Accordingly, they are useful as abortifacients. They are also useful for induction of menses during approximately the first two weeks of a missed menstrual period and accordingly are useful as contraceptive anti-fertility agents.

The PGA compounds and derivatives and salts thereof increase the flow of blood in the mammalian kidney, thereby increasing volume and electrolyte content of the urine. For that reason, PGA compounds are useful in managing cases of renal disfunction, especially in cases of severe impaired renal blood flow, for example, the hepatorena syndrom and early kidney transplant rejection. In case of excessive or inappropriate ADH antidiuretic hormone vasopressin secretion, the diuretic effect of thse compounds is even greater. In anephretic states, the vasopressin action of these compounds is especially useful. For that reason, these compounds are useful to promote and accelerate healing of skin which has been damaged, for example, by burns, wounds, and abrasions, and after surgery. These compounds are also useful to promote and accelerate adherence and growth of skin autografts, especially small, deep (Davis) grafts which are intended to cover skinless areas by subsequent outward growth rather than initially, and to retard rejection of homografts.

For these purposes, these compounds are preferably administered topically at or near the site where cell growth and keratin formation is desired, advantageously as an aerosol liquid or micronized powder spray, as an isotonic aqueous solution in the case of wet dressings, or as a lotion, cream, or ointment in combination with the usual pharmaceutically acceptable diluents. In some instances, for example, when there is substantial fluid loss as in the case of extensive burns or skin loss due to other causes, systemic administration is advantageous, for example, by intravenous injection or infusion, separate or in combination with the usual infusions of blood, plasma, or substituents thereof. Alternative routes of administration are subcutaneous or intramuscular near the site, oral, sublingual, buccal, rectal, or vaginal. The exact dose depends on such factors as the route of administration, and the age, weight, and condition of the subject. To illustrate a wet dressing for topical application to second and/or third degree burns of skin area 5 to 25 square centimeters would advantageously involve use of an isotonic aqueous solution containing 2 to 2000 μg/ml of the PGE compound. Especially for topical use, these prostaglandins are useful in combination with antibiotics, for example, gentamcyin, neomycin, polymyxin B, bacitracin, spectinomycin, and oxytetracycline, with other antibacterials, for example, mafenide hydrochloride, sulfadiazine, furazolium chloride, and nitrofurazone, and with corticoid steroids, for example, hydrocortisone, prednisolone, methylprednisolone, and fluoroprednisoline, each of those being used in combination at the usual concentrations suitable for its use alone.

Furthermore, some $PGE_1$ carbinols have been shown to act as specific gastric anti-secretory agents comparable to $PGE_1$ with low or undetectable side effects. Moreover, the carbinol dderivatives were found not to effect smooth muscle at doses at least 200 times those at which $PGE_1$ causes significant effects.

The novel compounds of this invention induce the biological responses described hereinabove as associated with its particular prostaglandin type. These novel compounds are accordingly used for the above-described corresponding purposes.

The novel PGE, $PGF_\beta$ and PGA compounds of this invention are also useful as bronchodialtors for the treatment of asthma and chronic bronchitis. As such they may be conveniently administered by inhalation of aerosol sprays prepared in a dose range of about 10 μg to about 10 mg/ml of a pharmacologically suitable liquid vehicle. Relative to the natural prostaglandins, the PGE compounds in particular have the significant advantage of inducing prolonged effects.

The invention will be described in greater detail in conjunction with the following specific examples.

EXAMPLE 1

Preparation of 4-Trimethylsiloxy-1-octyne

To a cold solution of 166 g of 4-hydroxy-1-octyne [Prostaglandins, 10, 289 (1975)], and 240 g of imidazole in one liter of dimethylformamide is added dropwise 202 g of chlorotrimethylsilane. The mixture is allowed to stand at room temperature for 2 to 3 days. The mixture is partitioned with water and hexane. The hexane layer is washed with brine, dried over magnesium sulfate, and concentrated. Distillation of the residue gives a colorless liquid, b.p. 38° (0.2 mm).

EXAMPLE 2

Preparation of 1-Iodo-4-Trimethylsiloxy-trans-1-octene

To a stirred solution of 0.20 moles of freshly prepared bis-(3-methyl-2-butyl)borane in 300 ml of tetrahydrofuran at 0°-5° C. is added dropwide a solution of 19.8 g of 4-trimethylsiloxy-1-octyne in 30 ml of tetrahydrofuran. The resulting mixture is stirred at ambient temperature for several hours, cooled in an ice bath, and treated with 53 g of trimethylamine oxide. The mixture is stirred several hours at 25°-40° C. and then poured into 2 liters of 15% sodium hydroxide. The resulting mixture is treated immediately with a solution of 140 g of iodine in 300 ml of tetrahydrofuran. After 0.5 hour the organic phase is separated and the aqueous phase is extraced with ether. The combined organic layers are washed with water, sodium thiosulfate solution, and concentrated to give an oil, pmr spectrum ($CDCl_3$): 6.2 (d, IC$\underline{H}$=) and 6.7 (quintuplet, =C$\underline{H}$-).

EXAMPLE 3

Preparation of 4-Hydroxy-1-iodo-trans-1-octene

A 23 g portion of 1-iodo-4-trimethylsiloxy-trans-1-octene is dissolved in a mixture of 200 ml of glacial acetic acid, 100 ml of tetrahydrofuran, and 50 ml of water. After solution occurs, toluene is added and the mixture is evaporated. The resulting oil is chromatographed on silica gel with hexane progressively enriched in benzene followed by acetone to give 16 g of an oil, pmr spectrum ($CDCl_3$): 3.69 (m, C$\underline{H}$OH) and 2.3 (s, O$\underline{H}$).

EXAMPLE 4

Preparation of 4-Oxo-1-iodo-trans-1-octene

To a stirred suspension of 6.15 g of pyridinium chlorochromate (Tetrahedron Letters 1975, 2647) in 20 ml of methylene chloride is added 450 mg of sodium acetate. After 5 minutes a solution of 3.64 g of 4-hydroxy-1-iodo-trans-1-octene in 15 ml of methylene chloride is added in one portion. The dark mixture is stirred at room temperature for 75 minutes, diluted with 50 ml of ether, and decanted. The solid sludge is washed repeatedly with ether and decanted. The combined solutions are percolated through Florisil. The solution is concentrated to give an orange liquid, pmr spectrum ($CDCl_3$): 3.20 (d, j=7 cps, =CHC$\underline{H}_2$CO).

EXAMPLE 5

Preparation of 4-Hydroxy-4-vinyl-1-iodo-trans-1-octene

To a stirred solution of 7.8 ml of vinyl magnesium chloride (2.3 M in tetrahydrofuran), at −25° C. is added a solution of 3.55 g of 4-oxo-1-iodo-trans-1-octene in 20 ml of tetrahydrofuran during 15 minutes. After the addition, the solution is stirred at −20° C. to −15° C. for 30 minutes. The reaction is quenched with a mixture of hexane and ice. The aqueous phase is separated and extracted with additional hexane. The combined hexane extracts are washed successively with water and brine. The solution is dried over magnesium sulfate and concentrated. The residue is subjected to dry column chromatography on silica gel with benzene as developing solvent to give a liquid, pmr spectrum ($CDCl_3$): 5.2 (m, terminal C$\underline{H}_2$), 5.83 (q, C$\underline{H}$=$CH_2$), 6.13 (d, IC$\underline{H}$=), and 6.52 (m, ICM=C$\underline{H}$).

EXAMPLE 6

Preparation of 4-Trimethylsiloxy-4-vinyl-1-iodo-trans-1-octene

To a stirred solution of 456 mg of 4-hydroxy-4-vinyl-1-iodo-trans-1-octene and 320 mg of imidazole in 1.0 ml of dimethylformamide is added 0.23 ml of chlorotrimethyl-silane during 3 minutes. The mixture is stirred at room temperature for 22 hours and partitioned with a mixture of cold hexane and water. The hexane layer is washed repeatedly with water and then brine, dried over magnesium sulfate, and concentrated to give an oil, pmr spectrum (CDCl$_3$): 0.13 (s, trimethylsiloxy group) and 2.32 (d, =CHC$\underline{H}_2$).

EXAMPLE 7

Preparation of 2,5-dihydro-2,5-dimethoxy-2-(8'-hydroxy-3'-cis-octenyl) furan To a stirred solution of 10 ml of 3.6 M sodium bis-(2-methoxyethoxy)aluminum hydride in toluene is slowly added a solution of 4.85 g of 2,5-dihydro-2,5-dimethoxy-2-(7'-carboxy-3'-cis-hexenyl)furan in 90 ml of toluene over an interval of 60 minutes, with the temperature maintained at 75° C. The mixture is then heated at 75° C. for 2 hours, cooled to 0° C. and diluted with 50 ml of ether. 20 ml of 20% aqueous sodium hydroxide is added dropwise to the mixture. The organic layer is separated, washed with saturated sodium chloride solution and dried over anhydrous potassium carbonate. The solvent is evaporated to provide the title compound.

EXAMPLE 8

Preparation of 2-(7'-hydroxy-2'-cis-heptenyl)-4-hydroxy cyclopent-2-en-1-one A stirred solution of 5.12 g of 2,5-dihydro-2,5-dimethoxy-2-(8'-hydroxy-3'-cis-octenyl)furan, 2.65 g of sodium dihydrogen phosphate monohydrate, 525 mg of anhydrous sodium acetate, and 20 mg of hydroquinone in 135 ml of dioxane and 68 ml of water is refluxed for 24 hours. The stirred solution is cooled to 50° C. and treated dropwise with 5.4 ml of concentrated sulfuric acid. The resulting solution is refluxed for 18 hours and then cooled to 25° C. Sodium chloride is added to form a saturated solution which is then extracted with ethyl acetate. The extract is washed with brine, dried over magnesium sulfate, and concentrated to afford the title compound.

EXAMPLE 9

Preparation of 4-1(1-methoxy-1-methylethoxy)-2-[7-(1-methoxy-1-methylmethoxyl)-heptyl]-cyclopent-2-en-1-one To a solution of 3.57 g of 4-hydroxy-2-(7-hydroxyheptyl)-cyclopent-2-en-1-one in 27 ml of methylene chloride, under a positive pressure of argon at 10°-15° C., is added rapidly by pipet 5.4 ml of methoxypropene. 0.1 ml of dichloroacetic acid is then added dropwise and the solution stirred at ambient temperature for 4 hours and addition of a few more drops of dichloroacetic acid causes no reaction. The solution is diluted with 250 ml of hexane and shaken with 200 ml of saturated sodium bicarbonate solution. The layers are separated. The aqueous phase is extracted twice with 100 ml each of hexane. The combined organic layers are washed with 250 ml of saturated sodium chloride solution and dried over sodium sulfate. The salt is filtered off and the solution concentrated under reduced pressure. The product is a yellow oil weighing about 4.6 g and used without further purification.

EXAMPLE 10

In the manner of Example 9, the 4-hydroxy-2-(7'-hydroxy-2'-cis-heptenyl)cyclopent-2-en-1-one of Example 8 can be converted to its corresponding alkoxyether, 4-(1-methoxy-1-methylmethoxy)-2-[1-methoxy-1-methylmethoxy)-2-cis-heptenyl]-cyclopent-2-en-1-one.

EXAMPLE 11-13

In the manner of Example 9, the following 4-hydroxy-(7'-hydroxy)-cyclopentenones in the art can be converted to their corresponding ethoxyethyethers by using ethylvinyl ether instead of methoxypropene.

| Example | Starting Cyclopentenone | Product 4-ethyoxethoxy-(7-ethoxy-ethoxy)cyclopent-2-en-1-one |
|---|---|---|
| 11 | 4-hydroxy-(7'-hydroxy-heptyl)-cyclopent-2-en-1-one | 4-ethoxyethoxy-(7'-ethoxy-ethoxypheptyl)-cyclopent-2-en-1-one |
| 12 | 4-hydroxy-(7'-hydroxy-2'-cis-heptenyl)-cyclopent-2-en-1-one | 4-ethoxyethoxy-(7'-ethoxy-ethoxy-2'-cis-heptenyl)-cyclopent-2-en-1-one |
| 13 | 4-hydroxy-2-(7'-hydroxy-2'-cis-nonenyl)-cyclopent-2-en-1-one | 4-ethoxyethoxy-(7-ethoxy-ethoxy-2'-cis-nonenyl)-cyclopent-2-en-1-one |

EXAMPLE 14

Preparation of 1,11α,16-trihydroxy-9-oxo-16-vinyl-13-trans-prostene

To a stirred solution of 555 mg of 4-trimethylsiloxy-4-vinyl-1-iodo-trans-1-octene in 2 ml of ether is added a solution of t-butyllithium in pentane (1.6 M 2eq.) during 10 minutes at −78° C. The solution is stirred at −78° C. for 1.5 hours and at −50° C. for 30 minutes to provide the 1-lithio-trans-alkene.

In a separate flask a mixture of 0.21 g of 1-copper-(I)-1-pentyne, 0.70 ml of hexamethylphosphorous triamide, and 2 ml of ether is stirred until a clear solution is obtained. This solution is added during 10 minutes to the stirred 1-lithio-trans-alkene solution at −78° C. The solution is stirred for 2 hours at −78° C. and then treated with a solution of 580 mg of 4-(1-methoxy-1-methylethoxy)-2-[7-(1-methoxy-1-methylethoxy)-heptyl]cyclopent-2-en-1-one in 3 ml of ether during 10 minutes. After 10 minutes at −78° C. the solution is stirred at −40° C. to −50° C. for one hour and at −35° C. to −30° C. for one hour. The solution is cooled to −50° C., poured into 100 ml of saturated ammonium chloride solution, and diluted with ether. The organic phase is separated, washed successively with water and dilute hydrochloric acid, and filtered through diatomaceous earth. The filtrate is washed successively with water and brine and dried over magnesium sulfate. Evaporation of solvent affords the crude bis-trimethylsilyl ether as an oil.

This oil is treated with a solution prepared from 10 ml of glacial acetic acid, 5 ml of tetrahydrofuran, and 2.5 ml of water. The mixture is stirred at room temperature for 30 minutes and diluted with 50 ml of toluene. After concentration at 33° C. in vacuo, the residue is subjected to chromatography on silica gel with 1% acetic acid in ethyl acetate to provide an oil, pmr spectrum (CDCl$_3$): 4.08 (q 11β-H), 5.1 (m, terminal C$\underline{H}_2$), 5.57 (m, trans C$\underline{H}$=C$\underline{H}$), and 5.89 (m, C$\underline{H}$=CH$_2$).

EXAMPLE 15

Preparation of n-butyl cyclopropyl ketone

To a vigorously-stirred solution of 31.0 g of cyclopropanecarboxylic acid in 330 ml of ether is added a solution of n-butyllithium (748 moles) in ca. 750 ml. of 2:1 ether-hexane during 1 hour at 5°–10° C. The resulting suspension is diluted with 300 ml of ether and stirred at room temperature for 2 hours and at reflux for 2 hours. The mixture is cooled and poured into several portions of 1:1 ice-4N hydrochloric acid. The etheral phases are combined and washed with brine, sodium carbonate solution, and brine. The extract is dried over magnesium sulfate and concentrated. The residue is distilled to provide a liquid, b.p. 102°–104° C. (80 mm), pmr spectrum (CDCl$_3$): ∫2.55 (triplet, —CH$_2$CO—).

EXAMPLE 16

Preparation of 4-Cyclopropyl-4-hydroxy-1-octyne

To a stirred, refluxing suspension of amalgam prepared from 6.2 g of magnesium and 50 mg of mercuric chloride suspended in 60 ml of ether is added a solution of a mixture of 30.4 g of n-butyl cyclopropyl ketone (Example 8) and 29.8 g of propargyl bromide in 65 ml of ether during 60 minutes. After reaction at reflux temperature for an additional 30 minutes, the mixture is cooled to 0° and treated with 35 ml of saturated ammonium chloride. The mixture is diluted with ether and filtered through Celite. The filtrate is washed with brine, dried over potassium carbonate, and concentrated. The residue is distilled to provide a liquid, b.p. 93°–94° C. (12 mm), pmr spectrums (CDCl$_3$): 0.43 (cyclopropyl hydrogens), 2.07 (triplet, H̲C≡C), and 2.44 (doublet C≡CC̲H̲$_2$).

EXAMPLE 17

Preparation of 4-Cyclopropyl-4-trimethylsiloxy-1-octyne

To a stirred solution of 27.8 g of 4-cyclopropyl-4-hydroxy-1-octyne (Example 9) and 33.3 g of imidazole in 130 ml of dimethylformamide at 5° C. is added 24 ml of chlorotrimethylsilane during 5 minutes. The solution is stirred at ambient temperature for 17 hours and then partitioned with 600 ml of hexane and 250 ml of ice-water. The hexane phase is separated and washed successively with water and brine. The solution is dried over magnesium sulfate and evaporated to give a liquid, pmr spectrum (CDCl$_3$): 0.12 (singlet, trimethylsiloxy group), 2.02 (triplet, H̲C≡C), and 2.45 (doublet, C≡CC̲H̲$_2$).

EXAMPLE 18

Preparation of 4-Cyclopropyl-4-trimethylsiloxy-1-(tri-n-butylstannyl)-trans-1-octene A stirred mixture of 23.8 g of 4-cyclopropyl-4-trimethylsiloxy-1-octyne (Example 10), 28 ml of tri-n-butyltin hydride, and 50 mg of azobisisobutyronitrile under nitrogen is heated to 85° C. After the resulting exothermic reaction subsides the mixture is heated at 130° C. for 1 hour. The crude product is evaporatively distilled to give a liquid, pmr spectrum (CDCl$_3$): 0.10 (trimethylsiloxy group), 2.33 (doublet, =CHC̲H̲$_2$), and 6.02 (vinyl hydrogens).

EXAMPLES 19–21

In the matter of Example 9 the following cyclopropyl alkyl ketones of Table 1 are prepared by reaction of the appropriate alkyllithium with cyclopropane-carboxylic acid.

TABLE 1

| Example | Alkyllithium | Product Cyclopropyl Alkyl Ketone |
|---|---|---|
| 19 | n-propyllithium | cyclopropyl n-propyl ketone |
| 20 | n-amyllithium | n-amyl cyclopropyl ketone |
| 21 | n-hexyllithium | cyclopropyl n-hexyl ketone |

EXAMPLES 22–25

The following vinyl ketones of Table 2 below are prepared by reaction of vinyllithium with the requisite carboxylic acids of the table according to a procedure well-known in the art [J.C. Floyd, Tetrahedron Letters, 2877 (1974)].

TABLE 2

| Example | Carboxylic Acid | Product Alkyl Vinyl Ketone |
|---|---|---|
| 22 | n-butyric acid | n-propyl vinyl ketone |
| 23 | n-valeric acid | n-butyl vinyl ketone |
| 24 | n-hexanoic acid | n-amyl vinyl ketone |
| 25 | n-heptanoic acid | n-hexyl vinyl ketone |

EXAMPLES 26–32

In the manner of Example 16 the following 4-substituted-1-alkyn-4-ols are prepared by reaction of propargyl magnesium bromide with ketones of Table 3 below.

Table 3

| Example | Starting Ketones of Example | Product-4-Substituted-1-alkyn-4-ol |
|---|---|---|
| 26 | 19 | 4-cyclopropyl-4-hydroxy-1-heptyne |
| 27 | 20 | 4-cyclopropyl-4-hydroxy-1-nonyne |
| 28 | 21 | 4-cyclopropyl-4-hydroxy-1-decyne |
| 29 | 22 | 4-hydroxy-4-vinyl-1-heptyne |
| 30 | 23 | 4-hydroxy-4-vinyl-1-octyne |
| 31 | 24 | 4-hydroxy-4-vinyl-1-nonyne |
| 32 | 25 | 4-hydroxy-4-vinyl-1-decyne |

EXAMPLES 33–39

In the manner in Example 17 the following 4-substituted-1-alkyn-4-ols of Table 4 below are converted to their corresponding trimethylsilyl ethers.

TABLE 4

| Example | 1-Alkyn-4-ol of Example | Product 4-Trimethylsiloxy-1-alkyne |
|---|---|---|
| 33 | 26 | 4-cyclopropyl-4-trimethylsiloxy-1-heptyne |
| 34 | 27 | 4-cyclopropyl-4-trimethylsiloxy-1-nonyne |
| 35 | 28 | 4-cyclopropyl-4-trimethylsiloxy-1-decyne |
| 36 | 29 | 4-trimethylsiloxy-4-vinyl-1-heptyne |
| 37 | 30 | 4-trimethylsiloxy-4-vinyl-1-octyne |
| 38 | 31 | 4-trimethylsiloxy-4-vinyl-1-nonyne |
| 39 | 32 | 4-trimethylsiloxy-4-vinyl-1-decyne |

EXAMPLES 40–46

In the manner of Example 8 the following 1-(tri-n-butylstannyl)-4-substituted-4-trimethylsiloxy-trans-1-alkenes are prepared by reaction of tri-n-butyltin hydride with the precursor 1-alkynes of Table 5 below.

TABLE 5

| Example | Starting 1-Alkyns of Example | Product 1-(tri-n-butylstannyl)-1-trans-alkene |
|---|---|---|
| 40 | 33 | 1-(tri-n-butylstannyl)-4-cyclopropyl-4-trimethylsiloxy-trans-1-heptene |
| 41 | 34 | 1-(tri-n-butylstannyl)-4-cyclopropyl-4-trimethylsiloxy-trans-1-nonene |
| 42 | 35 | 1-(tri-n-butylstannyl)-4-cyclopropyl-4-trimethylsiloxy-trans-1-decene |
| 43 | 36 | 1-(tri-n-butylstannyl)-4-vinyl-4-trimethylsiloxy-trans-1-heptene |
| 44 | 37 | 1-(tri-n-butylstannyl)-4-vinyl-4-trimethylsiloxy-trans-1-octene |
| 45 | 38 | 1-(tri-n-butylstannyl)-4-vinyl-4-trimethylsiloxy-trans-1-nonene |
| 46 | 39 | 1-(tri-n-butylstannyl)-4-vinyl-4-trimethylsiloxy-trans-1-decene |

EXAMPLE 47

Preparation of 9-oxo-1,11α,16-trihydroxy-16-vinyl 13-trans-prostene

To a stirred solution of 4.0 g of 4-vinyl-4-trimethoxylsiloxy-1-(tri-n-butylstannyl)-trans-1-octene (Example 12) in 5 ml of tetrahydrofuran, under argon, at −78° C. is added 4.9 ml of 1.64 M n-butyllithium in hexane, dropwise with good stirring, over 5 minutes. The resulting solution is stirred at −78° C. for 5 minutes, and then at −45° C. to −40° C. for 2½ hours. The solution is recooled to −78° C. A solution of 1.0 g of pentynylcopper in 3.3 g of distilled tri-n-butyl phosphine is prepared and diluted with 7 ml of anhydrous ether. This solution is cooled and slowly added to the reaction mixture over 5 minutes using 2 ml of ether as a rinse. The mixture is stirred at −78° C. for 2 hours. A cooled solution of 2.0 g of 4-(1-methoxy-1-methylmethoxy)-2-[7-(1-methoxy-1-methylmethoxy)-heptyl]cyclopen-2-en-1-one in 5 ml of anhydrous ether is added. Stirring is continued at −78° C. for 10 minutes and at −40° C. for 1 hour. The reaction mixture is allowed to warm to −23° C. for 30 minutes and then cooled to −78° C. and quenched by pouring the mixture into a cold mixture of 200 ml of saturated ammonium chloride, 1 ml acetic acid, and 100 ml of ether and stirred vigorously for 30 minutes.

The layers are separated and the aqueous layer is extracted with 100 ml ethyl acetate. The organic layers are combined and washed with 100 ml cold dilute 5% hydrochloric acid, 100 ml water and then a mixture of 100 ml of 50% saturated ammonium chloride and 100 ml of 50% saturated sodium chloride. The organic phase is dried over sodium sulfate and stored overnight under argon in the refrigerator. The solution is concentrated to a brown oil under reduced pressure. A hydrolysis solution consisting of 4 parts acetic acid, 2 parts tetrahydrofuran and 1 part water is prepared. 75 ml of the hydrolysis solution is added to the oil and the solution is stirred at 38° C. under argon for 1 hour. 50 ml of toulene is added and the solution is concentrated under reduced pressure at 38° C. 10 to 15 ml of toluene is added several times more during the concentration.

The resulting oil is dissolved in 25 ml methanol and washed twice with 25 ml each of heptane to remove most of the tri-n-butyl phosphine. The heptane washes are back extracted with a small amount of about 10 ml of methanol. The methanol extracts are combined and concentrated under reduced pressure to yield an oil.

A solution of 70 parts ethyl acetate, 30 parts heptane and 1 part methanol is prepared for use as an eluent. The oil is dissolved in 15 ml of the above solution and introduced to a dry column which is 66 inches long with a 3 inch internal diameter flexible dry column tubing packed with 1500 g of Woelm silica gel for dry columns. The column is eluted with a total of 2 liters of the eluent, 500 ml of which is collected. The retention volume of the column is 1.5 liters. A 24 inch section is removed from the bottom of the column, and then 36 one inch sections were cut. Fraction 2 contained 0.1 g of material which is approximately 50% cis and 50% trans product. Fractions 21–22 contained 0.3 g of material which is predominantly the trans product with some cis contaminant. 0.77 grams of pure trans material is obtained from fractions 23–25.

EXAMPLES 48–64

The product 9-oxo-11α,16-trihydroxy-prostadienes or prostenes of Table 6 below are obtained by the procedure described in Example 47. In accordance with the process described therein, the starting 1-(tri-n-butylstannyl)-4-trimethylsiloxy-trans-1-alkenes listed in Table 6 are treated with n-butyllithium to provide the corresponding trans-1-alkenyl lithium derivative which on treatment with copper pentyne-tri-n-butylphosphine complex furnish the corresponding trans-1-alkenylcuprates, which in turn are treated with the 4-oxycyclopent-2-en-1-ones listed in the table. The resulting 9-oxo-1,11α-bis(1-methoxy-1-methylethoxy)-16-trimethylsiloxy-prostadiene or prostene is hydrolyzed to the listed products by treatment with acetic acid-tetrahydrofuran-water.

TABLE 6

| Example | Starting cyclopentenone ether | Starting 1-(tri-n-butylstannyl)-4-trimethylsiloxy-trans-1-alkene of Example | Product 9-oxo-1,11α,16-trihydroxy-prostadiene or prostene |
|---|---|---|---|
| 48 | Example 9 or Example 11 | 40 | 9-oxo-1,11α,16-trihydroxy-16-cyclopropyl-20-nor-13-trans-prostene |
| 49 | Example 9 or Example 11 | 18 | 9-oxo-1,11α,16-trihydroxy-16-cyclopropyl-13-trans-prostene |
| 50 | Example 9 or Example 11 | 41 | 9-oxo-1,11α,16-trihydroxy-16-cyclopropyl-20-methyl-13-trans-prostene |
| 51 | Example 9 or Example 11 | 42 | 9-oxo-1,11α,16-trihydroxy-16-cyclopropyl-20-ethyl-13-trans- |

TABLE 6-continued

| Example | Starting cyclopentenone ether | Starting 1-(tri-n-butylstannyl)-4-trimethylsiloxy-trans-1-alkene of Example | Product 9-oxo-1,11α,16-trihydroxy-prostadiene or prostene |
|---|---|---|---|
| 52 | Example 9 or Example 11 | 43 | 9-oxo-1,11α,16-trihydroxy-16-vinyl-20-nor-13-trans-prostene |
| 53 | Example 9 or Example 11 | 44 | 9-oxo-1,11α,16-trihydroxy-16-vinyl-20-methyl-13-trans-prostene |
| 54 | Example 9 or Example 11 | 45 | 9-oxo-1,11α,16-trihydroxy-16-vinyl-20-ethyl-13-trans-prostene |
| 55 | Example 10 or Example 12 | 40 | 9-oxo-1,11α,16-trihydroxy-16-cyclopropyl-20-nor-5-cis,13-trans-prostadiene |
| 56 | Example 10 or Example 12 | 18 | 9-oxo-1,11α,16-trihydroxy-16-cyclopropyl-5-cis,13-trans-prostadiene |
| 57 | Example 10 or Example 12 | 41 | 9-oxo-1,11α,16-trihydroxy-16-cyclopropyl-20-methyl-5-cis,13-trans-prostadiene |
| 58 | Example 10 or Example 12 | 42 | 9-oxo-1,11α,16-trihydroxy-16-cyclopropyl-20-ethyl-5-cis,13-trans-prostadiene |
| 59 | Example 10 or Example 12 | 43 | 9-oxo-1,11α,16-trihydroxy-16-vinyl-20-nor-5-cis,13-trans-prostadiene |
| 60 | Example 10 or Example 12 | 44 | 9-oxo-1,11α,16-trihydroxy-16-vinyl-5-cis,13-trans-prostadiene |
| 61 | Example 10 or Example 12 | 45 | 9-oxo-1,11α,16-trihydroxy-16-vinyl-20-methyl-5-cis,13-trans-prostadiene |
| 62 | Example 10 or Example 12 | 46 | 9-oxo-1,11α,16-trihydroxy-16-vinyl-20-ethyl-5-cis,13-trans-prostadiene |
| 63 | Example 13 | (by procedure of Ex. 7) 6 | 9-oxo-1,11α,16-trihydroxy-16-vinyl-5-cis,13-trans-2a,2b-bishomoprostadiene |
| 64 | Example 13 | 18 | 9-oxo-1,11α,16-trihydroxy-16-cyclopropyl-5-cis,13-trans-2a,2b-bishomoprostadiene |

EXAMPLE 65

Preparation of 1, 9α, 11α, 16-tetrahydroxy-16-cyclopropyl-5-cis, 13-trans-prostadiene To a stirred solution of 785 mg of 9-oxo-1, 11α, 16-trihydroxy-16-cyclopropyl-5-cis,13-trans-prostadiene (Example 33) in 12 ml of tetrahydrofuran at −70° C. is added 12 ml of a 0.5 M solution of lithium perhydro-9b-boraphenalyl hydride in tetrahydrofuran. The solution is stirred at −78° C. for 30 minutes, warmed to 0° C. during 15 minutes, and treated with 0.6 ml of water. The mixture is partitioned with ether-potassium carbonate solution. The aqueous phase is acidified with hydrochloric acid and extracted with ethyl acetate. The extract is washed with water and brine, dried over magnesium sulfate, and concentrated. The resulting residue is subjected to dry column chromatography on silica gel with 1% acetic acid in ethyl acetate to provide a viscous oil.

EXAMPLES 66–83

Reduction of the 9-oxo-derivatives listed in the Table 7 below with lithium perhydro-9 b-boraphenalyl hydride by the method described in Example 65 provides the product 1, 9α-dihydroxy-prostadiene and prostene of the table.

TABLE 7

| Ex. | Starting 9-oxo-prostadien-1-ol or prosten-1-ol of Example | Product 9α,11α,16-trihydroxy-prostadien-1-ol or prosten-1-ol |
|---|---|---|
| 66 | 48 | 9α,11α,16-trihydroxy-16-cyclopropyl-20-nor-13-trans-prosten-1-ol |
| 67 | 49 | 9α,11α,16-trihydroxy-16-cyclopropyl-13-trans-prosten-1-ol |
| 68 | 50 | 9α,11α,16-trihydroxy-16-cyclopropyl-20-methyl-13-trans-prosten-1-ol |
| 69 | 51 | 9α,11α,16-trihydroxy-16-cyclopropyl-20-ethyl-13-trans-prosten-1-ol |
| 70 | 52 | 9α,11α,16-trihydroxy-16-vinyl-20-nor-13-trans-prosten-1-ol |
| 71 | 47 | 9α,11α,16-trihydroxy-16-vinyl-13-trans-prosten-1-ol |
| 72 | 53 | 9α,11α,16-trihydroxy-16-vinyl-20-methyl-13-trans-prosten-1-ol |
| 73 | 54 | 9α,11α,16-trihydroxy-16-vinyl-20-ethyl-13-trans-prosten-1-ol |
| 74 | 55 | 9α,11α,16-trihydroxy-16-cyclopropyl-20-nor-5-cis,13-trans-prostadien-ol |
| 75 | 56 | 9α,11α,16-trihydroxy-16-cyclopropyl-5-cis,13-trans-prostadien-1-ol |
| 76 | 57 | 9α,11α,16-trihydroxy-16-cyclopropyl-20-methyl-5-cis,13-trans-prostadien-1-ol |
| 77 | 58 | 9α,11α,16-trihydroxy-16-cyclopropyl-20-ethyl-5-cis,13-trans- |

TABLE 7-continued

| Ex. | Starting 9-oxo-prostadien-1-ol or prosten-1-ol of Example | Product 9α,11α,16-trihydroxy-prostadien-1-ol or prosten-1-ol |
|---|---|---|
| 78 | 59 | 9α,11α,16-trihydroxy-16-vinyl-20-nor-5-cis,13-trans-prostadien-1-ol |
| 79 | 60 | 9α,11α,16-trihydroxy-16-vinyl-5-cis,13-trans-prostadien-1-ol |
| 80 | 61 | 9α,11α,16-trihydroxy-16-vinyl-20-methyl-5-cis,13-trans-prostadien-1-ol |
| 81 | 62 | 9α,11α,16-trihydroxy-16-vinyl-20-ethyl-5-cis,13-trans-prostadien-1-ol |
| 82 | 63 | 9α,11α,16-trihydroxy-16-vinyl-5-cis-13-trans-2a,2b-bishomo-prostadien-1-ol |
| 83 | 64 | 9α,11α,16-trihydroxy-16-cyclopropyl-5-cis,13-trans-2a,2b-bishomoprostadien-1-ol |

EXAMPLE 84

Preparation of 9-oxo-1,16-dehydroxy-16-vinyl-5-cis,10,13-trans-prostatriene

To a stirred solution of 0.28 g of 9-oxo-11α,16-dihydroxy-16-vinyl-5-cis,13-trans-prostadien-1-ol (Example 47) in 25 ml of pyridine is added 2.7 ml of acetic anhydride. After standing for 5 hours at room temperature, the solution is stirred with a mixture of ethyl acetate and 1 M aqueous sodium bisulfate at 0° C. The ethyl acetate layer is washed with brine and concentrated in the presence of toluene.

The residue, consisting of crude 9-oxo-11α-acetoxy-16-hydroxy-16-vinyl-5-cis,13-trans-prostadien-1-ol, is dissolved in 20 ml of methanol with 1.2 g of potassium acetate. After standing for 18 hours at room temperature, the solution is partitioned with ethyl acetate and brine. The organic phase is washed with brine, dried over magnesium sulfate, and concentrated. The residue is purified by partition chromatography on Celite with the system heptane-dichloromethane-methanol-water (80:20:15:6) to give an oil.

EXAMPLES 85–101

Treatment of the 9-oxo-11α,16-dihydroxy prostadien-1-ol or prostene of Table 8 below with acetic anhydride in pyridine followed by potassium acetate in methanol according to Example 83 furnishes the product 9-oxo-16-hydroxy-Δ$^{10}$ prostadien-1-ol or prostatrien-1-ol of the table.

TABLE 8

| Ex. | Starting 9-oxo-11α16-dihydroxy prostadien-1-ol | Product 9-oxo-16-hydroxy-prostadien-1-ol or prostatrien-1-ol |
|---|---|---|
| 85 | 48 | 9-oxo-16-hydroxy-16-cyclopropyl-20-nor-10,13-trans-prostadien-1-ol |
| 86 | 49 | 9-oxo-16-hydroxy-16-cyclopropyl-10,13-trans-prostadien-1-ol |
| 87 | 50 | 9-oxo-16-hydroxy-16-cyclopropyl-20-methyl-10,13-trans-prostadien-1-ol |
| 88 | 51 | 9-oxo-16-hydroxy-16-cyclopropyl-20-ethyl-10,13-trans-prostadien-1-ol |
| 89 | 52 | 9-oxo-16-hydroxy-16-vinyl-20-nor-10,13-trans-prostadien-1-ol |
| 90 | 47 | 9-oxo-16-hydroxy-16-vinyl-10,13-trans-prostadien-1-ol |
| 91 | 53 | 9-oxo-16-hydroxy-16-vinyl-20-methyl-10,13-trans-prostadien-1-ol |
| 92 | 54 | 9-oxo-16-hydroxy-16-vinyl-20-ethyl-10,13-trans-prostadien-1-ol |

| Ex. | Starting 9-oxo-11α16-dihydroxy-prostadien-1-ol or prosten-1-ol | Product 9-oxo-16-hydroxy-prostadien-1-ol or prostatrien-1-ol |
|---|---|---|
| 93 | 55 | 9-oxo-16-hydroxy-16-cyclopropyl-20-nor-5-cis,10,13-trans-prostatrien-1-ol |
| 94 | 56 | 9-oxo-16-hydroxy-16-cyclopropyl-5-cis,10,13-trans-prostatrien-1-ol |
| 95 | 57 | 9-oxo-16-hydroxy-16-cyclopropyl-20-methyl-5-cis,10,13-trans-prostatrien-1-ol |
| 96 | 58 | 9-oxo-16-hydroxy-16-cyclopropyl-20-ethyl-5-cis,10,13-trans-prostatrien-1-ol |
| 97 | 59 | 9-oxo-16-hydroxy-16-vinyl-20-nor-5-cis,10,13-trans-prostatrien-1-ol |
| 98 | 61 | 9-oxo-16-hydroxy-16-vinyl-20-methyl-5-cis,10,13-trans-prostatrien-1-ol |
| 99 | 62 | 9-oxo-16-hydroxy-16-vinyl-20-ethyl-5-cis,10,13-trans-prostatrien-1-ol |

| Ex. | Starting 9-oxo-11α,16-dihydroxy-prostadien-1-ol or prosten-1-ol of Example | Product 9-oxo-16-hydroxy-prostadien-1-ol or prostatrien-1-ol |
|---|---|---|
| 100 | 63 | 9-oxo-16-hydroxy-16-vinyl-5-cis,10,13-trans-2a,2b-bishomoprostatrien-1-ol |
| 101 | 64 | 9-oxo-16-hydroxy-16-cyclopropyl-5-cis,10,13-trans-2a,2b-bishomoprostatrien-1-ol |

EXAMPLE 102

Preparation and separation of 1, 9α,11α, 16-tetrahydroxy-16-cyclopropyl-5-cis-13-trans-prostadien and 1,9α,11α, 16-tetrahydroxy-16-cyclopropyl-5-cis-13-trans-prostadiene To a stirred, ice-cold solution of 360 mg of 9-oxo-1,11α,16-trihydroxy-16-cyclopropyl-5-cis,13-trans-prostadiene (Example 47) in 50 ml of ethanol is added 40% mg of sodium borohydride in small portions during 1 minute. The mixture is stirred at 0° C. for 5 minutes and at ambient temperature for 1.5 hours. The bulk of the ethanol is evaporated at room temperature, and the residue is partitioned with cold dilute hydrochloric acid and ethyl acetate. The organic phase is separated and washed with water and brine, dried over magnesium sulfate and concentrated. The residue is subjected to chromatography on silica gel to give (first eluted) an oil 1,9β,11α,16-tetrahydroxy-16-cyclopropyl-5-cis,13-trans-prostadiene.

EXAMPLES 103–111

Treatment of the 9-oxo-prostaglandins of Table 9 below with sodium borohydride by the procedure of Example 102 followed by chromatography is productive of the 9α-hydroxy and 9β-hydroxy prostaglandins of the table.

TABLE 9

| Ex. | Starting 9-oxo-prostadien-1-ol or prosten-1-ol of Example | Product 9α/β,11,16-trihydroxy-prostadien-1-ol or prosten-1-ol |
|---|---|---|
| 103 | 48 | 9α/β,11α,16-trihydroxy-16-cyclopropyl-20-nor-13-trans-prosten-1-ol |
| 104 | 49 | 9α/β,11α,16-trihydroxy-16-cyclopropyl-13-trans-prosten-1-ol |
| 105 | 50 | 9α/β,11α,16-trihydroxy-16-cyclopropyl-20-methyl-13-trans-prosten-1-ol |
| 106 | 51 | 9α/β,11α,16-trihydroxy-16-cyclopropyl-20-ethyl-13-trans-prosten-1-ol |
| 107 | 52 | 9α/β,11α,16-trihydroxy-16-vinyl-20-nor-13-trans-prosten-1-ol |
| 108 | 47 | 9α/β,11α,16-trihydroxy-16-vinyl-13-trans-prosten-1-ol |
| 109 | 53 | 9α/β,11α,16-trihydroxy-16-vinyl-20-methyl-13-trans-prosten-1-ol |
| 110 | 54 | 9α/β,11α,16-trihydroxy-16-vinyl-20-ethyl-13-trans-prosten-1-ol |
| 111 | 55 | 9α/β,11α,16-trihydroxy-16-cyclopropyl-20-nor-5-cis,13-trans-prostadien-1-ol |
| 112 | 57 | 9α/β,11α,16-trihydroxy-16-cyclopropyl-20-methyl-5-cis,13-trans-prostadien-1-ol |
| 113 | 58 | 9α/β,11α,16-trihydroxy-16-cyclopropyl-20-ethyl-5-cis,13-trans-prostadien-1-ol |
| 114 | 59 | 9α/β,11α,16-trihydroxy-16-vinyl-20-nor-5-cis,13-trans-prostadien-1-ol |
| 115 | 60 | 9α/β,11α,16-trihydroxy-16-vinyl-5-cis-13-trans-prostadien-1-ol |
| 116 | 61 | 9α/β,11α,16-trihydroxy-16-vinyl-20-methyl-5-cis,13-trans-prostadien-1-ol |
| 117 | 62 | 9α/β,11α,16-trihydroxy-16-vinyl-20-ethyl-5-cis,13-trans-prostadien-1-ol |
| 118 | 63 | 9α/β,11α,16-trihydroxy-16-vinyl-5-cis-13-trans-2a,2b-bishomo-prostadien-1-ol |
| 119 | 64 | 9α/β,11α,16-trihydroxy-16-cyclopropyl-5-cis,13-trans-2a,2b-bis-homoprostadien-1-ol |

EXAMPLES 120–121

Treatment of the carbinol analogs of 11α-hydroxy-prostaglandin of Table 14 by the procedure of Pike et al., Journ. of Org. Chem., 84, 3552, 1974 is productive of the carbinol analogs of $\Delta^{8,12}$ prostaglandin of the Table.

TABLE 11

| Example | Starting 11α-hydroxy prostaglandin | Product $\Delta^{8,12}$ prostaglandins |
|---|---|---|
| 120 | 46 | 9-oxo-16-hydroxy-16-vinyl-$\Delta^{8,12}$ 5-cis,13-trans-prostatrien-1-ol |
| 121 | 48 | 9-oxo-16-hydroxy-16-cyclopropyl $\Delta^{8,12}$,13-trans-prostadien-1-ol |

EXAMPLE 122

Preparation of 1,11α,16-trihydroxy-9-oxo-16-vinyl-13,trans-prostene

To a solution of 9α,11α,16-trihydroxyl-16-vinyl-13,trans-prostene (Example 71) in dry acetone at −40° C. is added N-trimethylsilyldiethylamine according to the procedure of Yankee et al., J. Chem. Soc. Chem. Comm. page 1121 (1972).

The reaction mixture is diluted with ether. The ether extract is dried and concentrated in vacuo to provide 1,11α-trimethylsilyloxy-9α,16-dihydroxy-16-vinyl-13-trans-prostene.

The resulting bisilylated material is oxidized with Collen's agent in situ (prepared from $CrO_3$ and pyridine in methylene chloride) according to the above reference for 5 minutes at 25° C. The material is desilyated by treatment with a mixture of methanol, water and acetic acid 1:0.1:0.05) for about an hour.

The solvent is removed in vacuo and the product is purified on silica gel to provide 1,11α,16-trihydroxy-9-oxo-16-vinyl-13-trans-prostene.

EXAMPLE 123

Treatment of the PGFα compounds disclosed by Examples 66 to 83 according to the procedure disclosed by Example 122 provides the corresponding PGE compound on Table 12.

TABLE 12

| Ex. | Starting 9α hydroy-prostadien-1-ol or prosten-1-ol of Example | Product 9-oxo-11α,16-dihydroxy-prostadien-1-ol or prosten-1-ol |
|---|---|---|
| 123 | 66 | 9-oxo-11α,16-dihydroxy-16-cyclopropyl-20-nor-13-trans-prosten-1-ol |
| 124 | 67 | 9-oxo-11α,16-dihydroxy-16-cyclopropyl-13-trans-prosten-1-ol |
| 125 | 68 | 9-oxo-11α,16-dihydroxy-16-cyclopropyl-20-methyl-13-trans-prosten-1-ol |
| 126 | 69 | 9-oxo-11α,16-dihydroxy-16-cyclopropyl-20-ethyl-13-trans-prosten-1-ol |
| 127 | 70 | 9-oxo-11α,16-dihydroxy-16-vinyl-20-nor-13-trans-prosten-1-ol |
| 128 | 72 | 9-oxo-11α,16-dihydroxy-16-vinyl-20-methyl-13-trans-prosten-1-ol |
| 129 | 73 | 9-oxo-11α,16-dihydroxy-16-vinyl-20-ethyl-13-trans-prosten-1-ol |
| 130 | 74 | 9-oxo-11α,16-dihydroxy-16-cyclopropyl-20-nor-5-cis,13-trans-prostadien-o-ol |
| 131 | 75 | 9-oxo-11α,16-dihydroxy-16-cyclopropyl-5-cis,13-trans-prostadien-1-ol |
| 132 | 76 | 9-oxo-11α,16-dihydroxy-16-cyclopropyl-20-methyl-5-cis,13-trans-prostadien-1-ol |
| 133 | 77 | 9-oxo-11α,16-dihydroxy-16-cyclopropyl-20-ethyl-5-cis,13-trans-prostadien-1-ol |
| 134 | 78 | 9-oxo-11α,16-dihydroxy-16-vinyl-20-nor-5-cis,13-trans-prostadien-1-ol |
| 135 | 65 | 9-oxo-11α,16-dihydroxy-16-vinyl-5-cis,13-trans-prostadien-1-ol |
| 136 | 79 | 9-oxo-11α,16-dihydroxy-16-vinyl-5-cis,13-trans-prostadien-1-ol |
| 137 | 80 | 9-oxo-11α,16-dihydroxy-16-vinyl-20-methyl-5-cis,13-trans-prostadien-1-ol |
| 138 | 81 | 9-oxo-11α,16-dihydroxy-16-vinyl-20-ethyl-5-cis,13-trans-prostadien-1-ol |
| 139 | 82 | 9-oxo-11α,16-dihydroxy-16-vinyl-5-cis-13-trans-2a,2b-bishomo-prostadien-1-ol |
| 140 | 83 | 9-oxo-11α,16-dihydroxy-16-cyclopropyl-5-cis,13-trans-2a,2b-bis-homoprostadien-1=ol |

EXAMPLE 141

Preparation of
9-oxo-11α,16-dihydroxy-1-acetoxymethyl-16-vinyl-13-trans-prostene To a solution of 218 mg of 9-oxo-1,11α,16-trihydroxy-16-vinyl-13-trans-prostene in 1 ml of dry pyridine at 0° C. is added, dropwise, a solution of 58 mg (1 eq) of acetic anhydride in 0.6 ml of dry pyridine. After stirring at 0° C. for 18 hours, the reaction mixture is placed directly onto a silica-gel dry column (150 g silica-gel, 35"×1", equilibrated with 15 ml ETOAC) and developed with ethyl acetate. The column is segmented and the portions containing the product are eluted with ethyl acetate to afford 88 mg of the 1-acetyl prostanoid.

In accordance with the procedure described above, the carbinol analogs are treated with acetic anhydride, proprionic anhydride, n-butyric anhydride and n-valeric anhydride to give the 1-acetoxymethyl, 1-propanoyloxy methyl, 1-n-butanoyloxy methyl and 1-n-pentanoyloxy methylester analogs.

EXAMPLE 142

Treatment of 9-oxo-1,11α,16-trihydroxy-16-vinyl-13-trans-prostene or the individual optical isomers thereof with 1.1 eq of the following acid halides by the procedure of Example 122 provides the corresponding 1-substituted carboxyl prostanoic derivatives:

CARBOXYLIC HALIDES

Acetyl bromide
Acetyl chloride
O-Acetylmandelic acid chloride
O-Acetylisalicyloyl chloride
Acryloyl chloride
1-Adamantanecarboxylic acid chloride
p-Anisoyl chloride
Benzoyl bromide
Benzoyl chloride
4-Biphenylcarbonyl chloride
Bromoacetyl bromide
2-Bromobenzoyl chloride
4-Bromobenzoyl chloride
2-Bromo-2,2-diphenylacetyl bromide
2-Bromopropionyl chloride
3-Bromopropionyl chloride
p-tert,Butylacetyl chloride
tert-Butylacetyl chloride
Butyryl chloride
3-Carbomethoxypropionyl chloride
Chloroacetyl chloride
o-Chlorobenzoyl chloride
m-Chlorobenzyl chloride
p-Chlorobenzoyl chloride
4-Chlorobutyryl chloride
α-Chloro-α,α-diphenylacetyl chloride
p-(Chloroformyl)-phenyl methyl carbonate
α-Chlorophenylacetyl chloride
2-Chloropropionyl chloride
3-Chloropropionyl chloride
5-Chlorovaleryl chloride
Cinnamoyl chloride
Crotonyl chloride
4-Cyanobenzoyl chloride
Cyclobutanecarboxylic acid chloride
Cyclohexanecarboxylic acid chloride
Cyclopropanecarboxylic acid chloride
Decanoyl chloride
Dichloroacetyl chloride
2,4-Dichlorobenzoyl chloride
2,6-Dichlorobenzoyl chloride
3,4-Dichlorobenzoyl chloride
Diethylcarbamyl chloride
3,5-Dimethoxybenzoyl chloride
3,3-Dimethylacryloyl chloride
3,5-Dinitrobenzoyl chloride
Diphenylcarbamyl chloride trans-3,6-Endomethylene-1,2,3,6-tetrahydrophthaloyl chloride
2-Ethylhexanoyl chloride
Ethyl malonyl chloride
Ethyl oxalyl chloride
Ethyl succinyl chloride
o-Fluorobenzoyl chloride
m-Fluorobenzoyl chloride
p-Fluorobenzoyl chloride
2-Furoyl chloride
Hexanoyl chloride
Isobutyryl chloride
Isophthaloyl dichloride
Isovaleryl chloride
Itaconyl chloride
Lauroyl chloride
Methacryloyl chloride
Methoxyacetyl chloride
Methyl 4-(chloroformyl)-butyrate
Methyl oxalyl chloride
Myristoyl chloride
m-Nitrobenzoyl chloride
p-Nitrobenzoyl chloride
Nonanoyl chloride
5-Norbomene-2-carbonyl chloride
Octanoyl chloride
Palmitoyl chloride
Pentafluorobenzoyl chloride
Phenoxyacetyl chloride
Phenylacetyl chloride trans-2-Phenylcyclopropane-1-carboxylic acid chloride
Propionyl chloride
2-Quinoxaloyl chloride
Terephthaloyl chloride
O-Toluoyl chloride
m-Toluoyl chloride
p-Toluoyl chloride
3,4,5-Trimethoxybenzoyl chloride
Trimethylacetyl chloride
10-Undecenoyl chloride
Valeryl chloride

CARBOXYLIC ACID ANHYDRIDES

Acetic anhydride n-Butyric anhydride
2,2-dimethylglutaric anhydride
3,3-dimethylglutaric anhydride
2,3-dimethylglutaric anhydride
Heptafluorobutyric anhydride
Homophthalic anhydride
Maleic anhydride
3-methylglutaric anhydride
Methylsuccinic anhydride
Propionic anhydride
Succinic anhydride
3,3-tetramethylene glutaric anhydride
benzoic anhydride Phthalic anhydride
3-nitrophthalic anhydride
Tetrabromophthalic anhydride
Tetrachlorophthalic anhydride
dl-Camphoric anhydride
cis-1,2-Cyclobutanedicarboxylic anhydride
cis-1,2-Cyclohexanedicarboxylic anhydride
Hexahydro-4-methylphthalic anhydride
cis-1,2,3,6-Tetrahydrophthalic anhydride
3,4,5,6-Tetrahydrophthalic anhydride

EXAMPLE 143

9-oxo-11α,16-dihydroxy-16-vinyl-1-acetyloxymethyl-5-cis-13-trans-prostadiene

To a solution of 0.1 g of 9-oxo-1,11α,16-trihydroxy-16-vinyl-5-cis-13-trans prostadiene in 0.75 ml of pyridine is added 0.026 g of acetic anhydride. After standing overnight, the pyridine is removed at reduced pressure. The residue is chromatographed on a dry column of silica gel eluting with benzene-ethylacetate 1:1 to give 0.049 g of the product.

EXAMPLE 144

Treatment of 9-oxo-1,11α,16-trihydroxy-16-vinyl-5-cis,13-trans-prostadiene or the individual optical isomers thereof with 1.1 eq of the acid halides of Example 142, by the procedure of Example 143 provides the corresponding 1-substituted carboxyloxy prostanoic derivative.

EXAMPLE 145

Treatment of 9-oxo-1,11α,16-trihydroxy-16-cyclopropyl-13-trans-prostene, or the individual isomers thereof, with 1.1 eq of the acid halides or anhydrides listed in Example 142 by the procedures of Example 143 is productive of the corresponding 1-carboxymethyl prostane derivatives.

EXAMPLE 146

Treatment of 9-oxo-1,11α,16-trihydroxy-16-cyclopropyl-5-cis,13-trans-prostadiene, or the individual isomers thereof, with 1.1 eq of the acid halides or anhydrides listed in Example 142 by the procedure of Example 143 is productive of the corresponding 1-carboxymethyl prostane derivatives.

A 15-deoxy-16-hydroxy substituted prostaglandin consists of two dlracemates, i.e., 16α-hydroxyl and 16β-hydroxyl which are separable into the 16α- and 16β-epimers. A species claim wherein the stereochemistry of the C$_{16}$ carbon is not specified encompasses the nat. 16α- and nat. 16β-forms of the compound and the racemic mixtures thereof.

This invention has been described in terms of specific embodiments set forth in detail herein, but, it should be understood that these are by way of illustration only and that the invention is not necessarily limited thereto. Modifications and variations will be apparent from this disclosure and may be resorted to without departing from the spirit of this invention, as those skilled in the art will understand. Accordingly, such variations and modifications of the disclosed invention are considered to be within the purview and scope of this invention and the following claims.

What is claimed is:

1. An optically active compound of the formula:

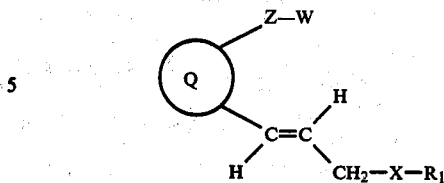

wherein Q is a divalent cyclopentyl moiety selected from the group consisting of:

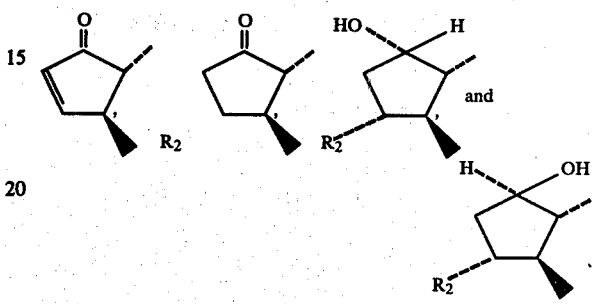

wherein $R_1$ is an alkyl ($C_3$-$C_7$) optionally substituted with one or more alkyl groups of one to three carbon atoms; $R_2$ is selected from the group comprising hydroxyl, alkoxyl, alkanoyloxy, a protecting group such as tetrahydropyran-2-yl-oxy, triloweralkylsilyloxy; or alkoxyalkoxy such as

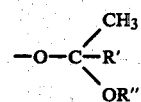

wherein R' is hydrogen or alkyl ($C_1$-$C_4$) and R'' is alkyl ($C_1$-$C_4$); X is a divalent radical

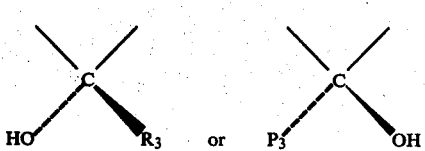

wherein $R_3$ is selected from the group comprising vinyl and cyclopropyl; Z is selected from the group consisting —(CH$_2$)$_4$ and

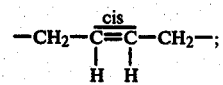

and W is selected from the group consisting of —(CH$_2$)$_3$—OH and

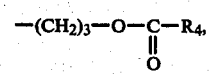

wherein $R_4$ is selected from the group comprising alkyl ($C_1$-$C_4$) alkoxy ($C_1$-$C_4$); dialkylamino ($C_1$-$C_4$); phenyl and phenyl substituted with one or more substituents selected from the group consisting of hydrogen, hydroxyl, lower alkyl, loweralkoxy, loweralkylthia, fluoride or chloride, wherein loweralkyl is $C_1$-$C_4$; the racemic mixtures thereof, the mirror images thereof.

2. A compound according to claim 1 wherein Q is

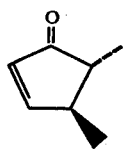

and Z is

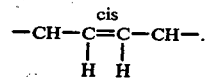

3. A compound according to claim 2 wherein W is —(CH$_2$)$_3$—OH and Z is —(CH$_2$)$_4$—.

4. A compound according to claim 2 wherein W is —(CH$_2$)$_3$—OH and Z is

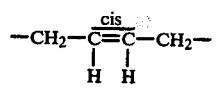

5. A compound according to claim 2 wherein W is

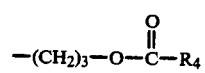

and Z is —(CH$_2$)$_4$—.

6. A compound according to claim 2 wherein W is

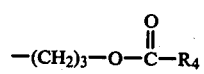

and Z is

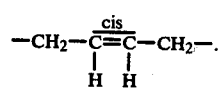

7. A compound according to claim 1 wherein Q is

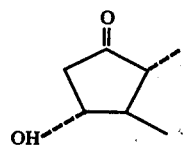

8. A compound according to claim 7 wherein W is —(CH$_2$)$_3$—OH and Z is —(CH$_2$)$_4$—.

9. A compound according to claim 7 wherein W is —(CH$_2$)$_3$—OH and Z is

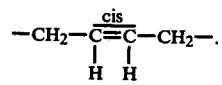

10. A compound according to claim 7 wherein W is

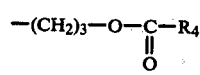

and Z is —(CH$_2$)$_4$—.

11. A compound according to claim 7 wherein W is

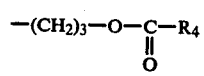

12. A compound according to claim 1 wherein Q is

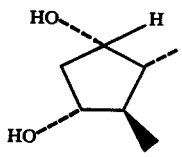

13. A compound according to claim 12 wherein W is —(CH$_2$)$_3$—OH and Z is —(CH$_2$)$_4$—.

14. A compound according to claim 12 wherein W is —(CH$_2$)$_3$—OH and Z is

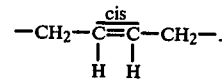

15. A compound according to claim 12 wherein W is

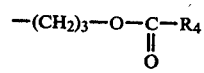

and Z is —(CH$_2$)$_4$—.

16. A compound according to claim 12 wherein W is

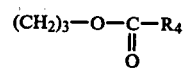

and Z is

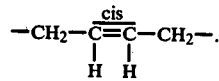

17. A compound according to claim 1 wherein Q is

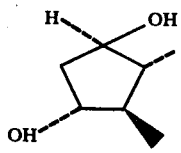

18. A compound according to claim 17 wherein W is —(CH$_2$)$_3$—OH and Z is —(CH$_2$)$_4$—.

19. A compound according to claim 17 wherein W is —(CH$_2$)$_5$ OH and Z is

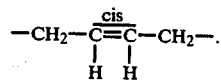

20. A compound according to claim 17 wherein W is

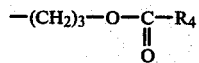

and Z is —(CH$_2$)$_4$—.

21. A compound according to claim 17 wherein W is

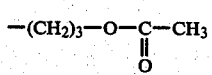

and Z is

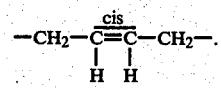

22. A compound according to claim 8, 1,11α,16-trihydroxy-9-oxo-16-vinyl-13-trans-prostene.

23. A compound according to claim 9, 1,11α,16-trihydroxy-9-oxo-16-vinyl-5-cis,13-trans-prostadiene.

24. A compound according to claim 8, 1,11α,16-trihydroxy-9-oxo-16-cyclopropyl-13-trans-prostene.

25. A compound according to claim 9, 1,11α,16-trihydroxy-9-oxo-16-cyclopropyl-5-cis,13-trans-prostadiene.

26. A compound according to claim 8, nat-1,11α,16α-trihydroxy-9-oxo-16-vinyl-13-trans-prostene.

27. A compound according to claim 9, nat-1,11α,16α-trihydroxy-9-oxo-16-vinyl-5-cis,13-trans-prostadiene.

28. A compound according to claim 8, nat-9-oxo-1,11α,16-trihydroxy-16-cyclopropyl-13-trans-prostene.

29. A compound according to claim 9, nat-9-oxo-1,11α,16-trihydroxy-16-cyclopropyl-5-cis,13-trans-prostadiene.

30. A compound according to claim 8, nat-9-oxo-1,11α,16β-trihydroxy-16-vinyl,13-trans-prostene.

31. A compound according to claim 9, nat-9-oxo-1,11α,16β-trihydroxy-16-vinyl-5-cis,13-trans-prostadiene.

32. A compound according to claim 8, nat-9-oxo-1,11α,16β-trihydroxy-16-cyclopropyl-13-trans-prostene.

33. A compound according to claim 9, nat-9-oxo-1,11α,16β-trihydroxy-16-cyclopropyl-5-cis,13-trans-prostadiene.

34. The compound according to claim 13, 1,9α,11α,16-tetrahydroxy-16-vinyl-13-trans-prostene.

35. The compound according to claim 14, 1,9α,11α,16-tetrahydroxy-16-vinyl-5-cis,13-trans-prostadiene.

36. The compound according to claim 13, 1,9α,11α,16-tetrahydroxy-16-cyclopropyl-13-trans-prostene.

37. The compound according to claim 14, 1,9α,11α,16-tetrahydroxy-16-cyclopropyl-5-cis,13-trans-prostadiene.

* * * * *